United States Patent [19]
Wong et al.

[11] Patent Number: 5,866,579
[45] Date of Patent: Feb. 2, 1999

[54] IMIDAZOLE AND IMIDAZOLINE DERIVATIVES AND USES THEREOF

[75] Inventors: Wai C. Wong, Newark; Yoon T. Jeon, Ridgewood, both of N.J.; T. G. Murali Dhar, Newark, Del.; Charles Gluchowski, Danville, Calif.

[73] Assignee: Synaptic Pharmaceutical Corporation, Paramus, N.J.

[21] Appl. No.: 834,658

[22] Filed: Apr. 11, 1997

[51] Int. Cl.$^6$ .................. A61K 31/47; A61K 31/505; C07D 401/06; C07D 403/06
[52] U.S. Cl. .................. 514/259; 514/307; 514/309; 514/312; 514/314; 514/398; 514/397; 514/313; 514/300; 546/141; 546/142; 546/146; 546/147; 546/153; 546/155; 546/156; 546/157; 546/167; 546/173; 546/176; 546/163; 546/112; 546/122; 546/114; 546/115; 544/284
[58] Field of Search ................. 546/148, 141, 546/142, 146, 147, 153, 155, 156, 157, 167, 173, 176; 514/307, 309, 312, 314, 259; 544/284

[56] References Cited

U.S. PATENT DOCUMENTS

| 5,028,606 | 7/1991 | Venet et al. | 514/249 |
|---|---|---|---|
| 5,663,189 | 9/1997 | Maurer et al. | 514/397 |

FOREIGN PATENT DOCUMENTS

| 2206880 | 1/1989 | United Kingdom . |
|---|---|---|
| 9214453 | 9/1992 | WIPO . |

OTHER PUBLICATIONS

Amemiya, Y., et al. "Synthesis and α–Adrenergic Activities of 2–and 4–Substituted Imidazoline and Imidazole Analogues" J. Med. Chem. (1992) 35: 750–755.

Hong, S., et al. "A Structure–Activity Relationship Study of Benzylic Modifications of 4–[1–(1–Napththyl) ethyl]–1H–imidazoles on $α_1$–and $α_2$–Adrenergic Receptors" J. Med. Chem. (1994) 37: 2328–2333.

Wong, W.C. et al., "Design and Synthesis of Alpha$_2$ Adrenoceptor Agonists" 213th American Chemical Society Meeting, San Francisco, CA , Apr. 13–17 (1997) MEDI No. 023.

Primary Examiner—Mukund J. Shah
Assistant Examiner—Ann M. Kessinger
Attorney, Agent, or Firm—John P. White; Cooper & Dunham LLP

[57] ABSTRACT

This invention is directed to novel imidazole and imidazoline derivatives which are selective agonists for cloned human $α_2$ adrenergic receptors. This invention is also related to the use of these compounds for the treatment of any disease where modulation of the $α_2$ receptors may be useful. The invention further provides for a pharmaceutical composition comprising a therapeutically effective amount of the above-defined compounds and a pharmaceutically acceptable carrier.

8 Claims, No Drawings

IMIDAZOLE AND IMIDAZOLINE DERIVATIVES AND USES THEREOF

BACKGROUND OF THE INVENTION

Throughout this application, various references are referred to within parentheses. Disclosure of these publications in their entireties are hereby incorporated by reference into this application to more fully describe the state of the art to which this invention pertains.

α-Adrenergic receptors (Lomasney, J. W. et al, *Biochim. Biophy. Acta* 1991, 1095, 127) are cell membrane proteins located in both the peripheral and central nervous systems. They belong to a diverse family of structurally related receptors which contain seven putative transmembrane helices and couple to intracellular guanine nucleotide binding proteins (G-proteins). These receptors are important switches for controlling many physiological functions and, thus, represent important targets for drug development. In fact, many α-adrenergic drugs have been developed over the past 40 years. Examples include clonidine, phenoxybenzamine and prazosin (for treatment of hypertension), naphazoline (for nasal decongestion), medetomidine (for veterinary analgesia), UK-14,304 and apraclonidine (for glaucoma). α-Adrenergic drugs canr be divided into two disinct classes: agonists (like clonidine and naphazoline) which mimic the receptor activation properties of the endogenous neurotransmitter norepinephrine, and antagorists (like phenoxybenzamine and prazosin) which act to block the effects of norepinephrine. However, many of these drugs, though effective, also produce undesirable side effects. For example, clonidine produces dry mouth and sedation in addition to its antihypertensive effects.

Prior to 1977, only one α-adrenergic receptor was known to exist. Between 1977 and 1988, it was accepted by the scientific community that at least two α-adrenergic receptors $α_1$ and $α_2$ existed. Since 1988, new techniques in molecular biology have led to the identification of at least six α-adrenergic receptors—$a_{1a}$, $α_{1b}$, $α_{1c}$, $α_{2a}$, $α_{2b}$ and $α_{2c}$ (Bylund, D. B., *FASEB J.* 1992, 6, 832). In addition, current $α_2$-adrenergic drugs are not selective for any particular $α_2$-adrenergic receptor subtype. This lack of selectivity likely contributes to the untoward side effect of these drugs.

$α_2$ receptors are located both presynaptically at nerve terminals and postsynaptically as in vascular smooth muscles, platelets, pancreatic β-cells, and fat cells. Activation of the presynaptic receptors inhibit the release of norepinephrine by a negative feedback mechanism. Blockade of these receptors would therefore increase the release of norepinephrine.

It is believed that $α_2$ receptors can modulate pain. Indeed, the effects of $α_2$ agonists on analgesia, anesthesia and sedation have been well documented (Pertovaara, P., *Progress in Neurobiology*, 1993, 40, 691). For example, systemic administration of clonidine has been shown to produce antinociception in various species including human patients in addition to its well known sedative effects. Intrathecal and epidural administration of clonidine has also proved effective in producing analgesia. Another agonist, medetomidine, which has better $α_2/α_1$ selectivity and is more potent at $α_2$ receptors than clonidine, has been shown in humans to be effective for ischemic pain even though the doses were high enough to produce sedation and considerable decrease in blood pressure.

However, in anesthetic practice, the sedative effect of $α_2$ agonists is regarded as a good component of premedication. Another beneficial effect of $α_2$ agonists is their ability to potentiate the anesthetic action and hence to reduce the anesthetic requirements of other agents during surgery (Ghingnone, M. et al., *Anesthesiology* 1986, 64, 36).

Other potential uses of $α_2$ agonists including lowering intraocular pressure, treating hypertension, alcohol and drug withdrawal, rheumatoid arthritis, ischemia migraine, cognitive deficiency, spasticity, diarrhea and nasal congestion (Cossement, E. et al., U.S. Pat. No. 4,923,865, 1990).

This invention is directed to imidazole and midazoline compounds which are selective agonists for human $α_2$ receptors. This invention is also related to the use of these compounds for treating disorders involving inhibition or lack of activation of $α_2$ adrenergic receptors such as hypertension, pain, glaucoma, alcohol and drug withdrawal, rheumatoid arthritis, ischemia, migraine, cognitive deficiency, spasticity, diarrhea and nasal congestion.

SUMMARY OF THE INVENTION

This invention is directed to imidazole and midazoline compounds which are selective agonists for human a receptors. This invention is also related to the use of these compounds for treating disorders involving inhibition or lack of activation of $α_2$ adrenergic receptors such as hypertension, pain, glaucoma, alcohol and drug withdrawal, rheumatoid arthritis, ischemia, migraine, cognitive deficiency, spasticity, diarrhea and nasal congestion. The invention further provides a pharmaceutical omposition comprising a therapeutically effective amount of the above-defined compounds and a pharmaceutically acceptable carrier.

The present invention provides a compound having the structure:

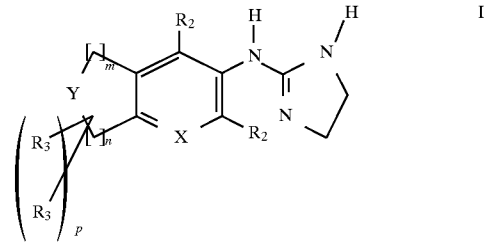

wherein X is $CR_7$; N; or $N^+O^-$;

wherein Y is O; CO; S; $CR_3R_5$; or $NR_6$;

wherein each $R_2$ is independently H; F; Cl; Br; I; —NO—, —CN; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —OH; —$(CH_2)_qOH$; —$COR_4$; $CO_2R_4$; $CONHR_4$; phenyl; or benzyl;

wherein each $R_3$ is independently H; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —$(CH_2)_qOH$; —OH; =N—$OR_4$; $COR_4$; $CO_2R_4$; $CONHR_4$; phenyl; or benzyl;

wherein each $R_4$ is independently H; straight chained or branched $C_1$–$C_4$ alkyl, $C_1$–$C_4$ monofluoroalkyl or $C_1$–$C_4$ polyfluoroalkyl; or phenyl;

wherein each $R_5$ is independently H; straight chained or branched $C_1$–$C_4$ alkyl, $C_1$–$C_4$ monofluoroalkyl, or $C_1$–$C_4$polyfluoroalkyl;

wherein $R_6$ is H; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —$CH_2CH_2(CH_2)_qOH$; $COR_4$; $CO_2R_4$; $CONHR_4$; phenyl; or benzyl;

wherein each $R_7$ is independently H; —CN; straight chained or branched $C_1$-$C_4$ alkyl; $C_1$-$C_4$ monofluoroalkyl: or $C_1$-$C_4$ polyfluoroalkyl; straight chained or branched $C_1$-$C_4$ alkoxy; —OH; —$(CH_2)_qOH$; —$COR_4$; $CO_2R_4$; $CONHR_4$; phenyl; or benzyl;

wherein m and n are each independently 0, 1, 2 or 3, provided that m+n is 2 or 3;

wherein each p is independently 0, 1 or 2; and wherein each q is independently 0, 1, 2 or 3;

or a pharmaceutically acceptable salt thereof.

The present invention also provides a compound having the structure:

[Chemical structure with R1, Z1, Z2, Z3, N]

wherein each of Z1, Z2 and Z3 is N or $CR_2$, with the proviso that either one of Z1, Z2 or Z3 is N and the otters of Z1, Z2 or Z3 are $CR_2$, or both Z1 and Z3 are N and Z2 is $CR_2$;

wherein $R_1$ is H; F; straight chained or branched $C_1$-$C_4$ alkyl, $C_1$-$C_4$ monofluorcalkyl $C_1$-$C_4$ polyfluoroalkyl; straight chained or branched $C_1$-$C_4$ alkoxy, —OH; or —$(CH_2)_qOH$;

wherein each $R_2$ is independently H; F; Cl; Br; I; —NO—, —CN; straight chained or branched $C_1$-$C_4$ alkyl; $C_1$-$C_4$ monofluoroalkyl or $C_1$-$C_4$ polyfluoroalkyl; straight chained or branched $C_1$-$C_4$ alkoxy; —OH; —$(CH_2)_qOH$; —COR; $CO_2R_4$; $CONHR_4$; phenyl; or benzyl;

wherein each $R_4$ is independently H; straight chained or branched $C_1$-$C_4$ alkyl, $C_1$-$C_4$ monofluoroalkyl or $C_1$-$C_4$ polyfluoroalkyl; or phenyl; and wherein q is each independently 0, 1, 2 or 3;

or a pharmaceutically acceptable salt thereof.

The present invention also provides a pharmaceutical composition comprising a therapeutically effective amount of the compounds described herein and a pharmaceutically acceptable carrier.

The present invention further provides a method for treating an $\alpha_2$ adrenergic receptor associated disorder in a subject, which comprises administering to the subject an amount of a compound effective to treat the disorder, wherein the compound has the structure:

[Chemical structure with R2, R3, X, Y, N, H]

wherein X is $CR_7$; N; or $N^+O^-$;

wherein Y is O; CO; S; $CR_3R_5$; or $NR_6$;

wherein each $R_2$ is independently H; F; Cl; Br; I; —$NO_2$, —CN; straight chained or branched $C_1$-$C_4$ alkyl; $C_1$-$C_4$ monofluoroalkyl or $C_1$-$C_4$ polyfluoroalkyl; straight chained or branched $C_1$-$C_4$ alkoxy; —OH; —$(CH_2)_qOH$; —$COR_4$; $CO_2R_4$; $CONHR_4$; phenyl; or benzyl;

wherein each $R_3$ is independently H; straight chained or branched $C_1$-$C_4$ alkyl; $C_1$-$C_4$ monofluoroalkyl or $C_1$-$C_4$ polyfluoroalkyl; straight chained or branched $C_1$-$C_4$ alkoxy; —$(CH_2)_qOH$; —OH; =N—$OR_4$; $COR_4$; $CO_2R_4$; $CONHR_4$; phenyl; or benzyl;

wherein each $R_4$ is independently H; straight chained or branched $C_1$-$C_4$ alkyl, $C_1$-$C_4$ monofluoroalkyl or $C_1$-$C_4$ polyfluoroalkyl; or phenyl;

wherein each $R_5$ is independently H; straight chained or branched $C_1$-$C_4$ alkyl, $C_1$-$C_4$ monofluoroalkyl, or $C_1$-$C_4$ polyfluoroalkyl;

wherein $R_6$ is H; straight chained or branched $C_1$-$C_4$ alkyl; $C_1$-$C_4$ monofluoroalkyl or $C_1$-$C_4$ polyfluoroalkyl; straight chained or branched $C_1$-$C_4$ alkoxy; —$CH_2CH_2(CH_2)_qOH$; $COR_4$; $CO_2R_4$; $CONHR_4$; phenyl; or benzyl;

wherein each $R_7$ is independently H; —CN; straight chained or branched $C_1$-$C_4$ alkyl; $C_1$-$C_4$ monofluoroalkyl or $C_1$-$C_4$ polyfluoroalkyl; straight chained or branched $C_1$-$C_4$ alkoxy; —OH; —$(CH_2)_qOH$; —$COR_4$; $CO_2R_4$; $CONHR_4$; phenyl; or benzyl;

wherein m and n are each independently 0, 1, 2 or 3, provided that m+n is 2 or 3;

wherein each p is independently 0, 1 or 2; and wherein each q is independently 0, 1, 2 or 3;

or a pharmaceutically acceptable salt thereof.

The present invention additionally provides a method for treating an $\alpha_2$ adrenergic receptor associated disorder in a subject, which comprises administering to the subject an amount of a compound effective to treat the disorder, wherein the compound has the structure:

[Chemical structure with R1, Z1, Z2, Z3, N]

wherein each of Z1, Z2 and Z3 is N or $CR_2$, with the proviso that either one of Z1, Z2 or Z3 is N and the otiers of Z1, Z2 or Z3 are $CR_2$, or both Z1 and Z3 are N and Z2 is $CR_2$;

wherein $R_1$ is H; F; straight chained or branched $C_1$-$C_4$ alkyl, $C_1$-$C_4$ monofluoroalkyl or $C_1$-$C_4$ polyfluoroalkyl; straight chained or branched $C_1$-$C_4$ alkoxy, —OH; or —$(CH_2)_qOH$;

wherein each $R_2$ is independently H; F; Cl; Br; I; —$NO_2$, —CN; straight chained or branched $C_1$-$C_4$ alkyl; $C_1$-$C_4$ monofluoroalkyl or $C_1$-$C_4$ polyfiuoroalkyl; straight chained or branched $C_1$-$C_4$ alkoxy; —OH; —$(CH_2)_qOH$; —$COR_4$; $CO_2R_4$; $CONHR_4$; phenyl; or benzyl;

wherein each $R_4$ is independently H; straight chained or branched $C_1$-$C_4$ alkyl, $C_1$-$C_4$ monofluoroalkyl or $C_1$-$C_4$ polyfluoroalkyl; or phenyl; and wherein q is each independently 0, 1, 2 or 3;

or a pharmaceutically acceptable salt thereof.

The present invention also provides a method for treating pain in a subject, which comprises administering to the subject an amount of a compound effective to treat the subject's pain, wherein the compound has the structure:

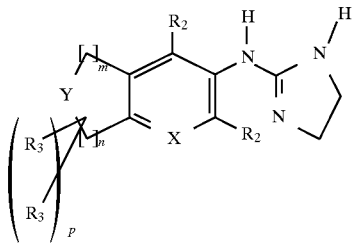

wherein X is $CR_7$; N; or $N^+O^-$;

wherein Y is O; CO; S; $CR_3R_5$; or $NR_6$;

wherein each $R_2$ is independently H; F; Cl; Br; I; —NO, —CN; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —OH; —$(CH_2)_qOH$; —$COR_4$; $CO_2R_4$; $CONHR_4$; phenyl; or benzyl;

wherein each $R_3$ is independently H; straight chained or branched $C_1$–$C_4$ alkyl; $C_1$–$C_4$ monofluoroalky or $C_1$–$C_4$ polyfluoroalkyl; straight chained or branched $C_1$–$C_4$ alkoxy; —$(CH_2)_qOH$; —OH; =N—$OR_4$; $COR_4$; $CO_2R_4$; $CONHR_4$; phenyl; or benzyl;

wherein each $R_4$ is independently H; straight chained or branched $C_1$–$C_4$ alkyl, $C_1$–$C_4$ monofluoroalky or $C_1$–$C_4$ polyfluoroalkyl; or phenyl;

wherein each $R_5$ is independently H; straight chained or branched $C_1$–$C_4$ alkyl, $C_1$–$C_4$ monofluoroalkyl or $C_1$–$C_4$ polyfluoroalkyl;

wherein $R_6$ is H; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —$CH_2CH_2(CH_2)_qOH$; $COR_4$; $CO_2R_4$; $CONHR_4$; phenyl; or benzyl;

wherein each $R_7$ is independently H; —CN; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —OH; —$(CH_2)_qOH$; —$COR$,; $CO_2R_4$; $CONHR_4$; phenyl; or benzyl;

wherein m and n are each independently 0, 1, 2 or 3, provided that m+n is 2 or 3;

wherein each p is independently 0, 1 or 2; and wherein each q is independently 0, 1, 2 or 3;

or a pharmaceutically acceptable salt thereof.

The present invention provides a method for treating pain in a subject, which comprises administering to the subject an amount of a compound effective to treat the subject's pain, wherein the compound has the structure:

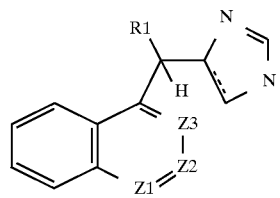

wherein each of Z1, Z2 and Z3 is N or $CR_2$, with the proviso that either one of Z1, Z2 or Z3 is N and the others of Z1, Z2 or Z3 are $CR_2$, or both Z1 and Z3 are N and Z2 is $CR_2$;

wherein $R_1$ is H; F; straight chained or branches $C_1$–$C_4$ alkyl, $C_1$–$C_4$ monofluoroalkyl or $C_1$–$C_4$ polyfluoralkyl; straight chained or branched $C_1$–$C_4$ alkoxy, —OH; or —$(CH_2)_qOH$;

wherein each $R_2$ is independently H; F; Cl; Br; I; —$NO_2$, —CN; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —OH; —$(CH_2)_qOH$; —$COR_4$; $CO_2R_4$; $CONHR_4$; phenyl; or benzyl;

wherein each $R_4$ is independently H; straight chained or branched $C_1$–$C_4$ alkyl, $C_1$–$C_4$ monofluoroalkyl or $C_1$–$C_4$ polyfluoroalkyl; or phenyl; and wherein q is each independently 0, 1, 2 or 3;

or a pharmaceutically acceptable salt thereof.

DETAILED DESCRIPTION OF THE INVENTION

The present invention is directed to compounds having the structure:

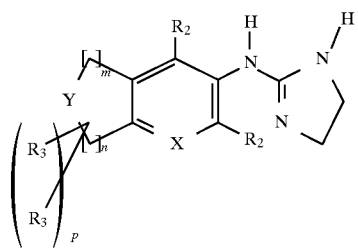

wherein X is $CR_7$; N; or $N^+O^-$;

wherein Y is O; CO; S; $CR_3R_5$; or $NR_6$;

wherein each $R_2$ is independently H; F; Cl; Br; I; —NO, —CN; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —OH; —$(CH_2)_qOH$; —$COR_4$; $CO_2R_4$; $CONHR_4$; phenyl; or benzyl;

wherein each $R_3$ is independently H; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —$(CH_2)_qOH$; —OH; =N—$OR_4$; $COR_4$; $CO_2R_4$; $CONHR_4$; phenyl; or benzyl ;

wherein each $R_4$ is independently H; straight chained or branched $C_1$–$C_4$ alkyl, $C_1$–$C_4$ monofluoroalkyl or $C_1$–$C_4$ polyfluoroalkyl; or phenyl;

wherein each $R_5$ is independently H; straight chained or branched $C_1$–$C_4$ alkyl, $C_1$–$C_4$ monofluoroalkyl or $C_1$–$C_4$ polyfluoroalkyl;

wherein $R_6$ is H; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —$CH_2CH_2(CH_2)_qOH$; $COR_4$; $CO_2R_4$; $CONHR_4$; phenyl; or benzyl;

wherein each $R_7$ is independently H; —CN; straight chained or branched $C_1$–$C_4$ alkyl; $C_1$–$C_4$ monofluoroalky or $C_1$–$C_4$ polyfluoroalkyl; straight chained or branched $C_1$–$C_4$ alkoxy; —OH; —$(CH_2)_qOH$; —$COR_4$; $CO_2R_4$; $CONHR_4$; phenyl; or benzyl;

wherein m and n are each independently 0, 1, 2 or 3, provided that m+n is 2 or 3;

wherein each p is independently 0, 1 or 2; and wherein each q is independently 0, 1, 2 or 3;

or a pharmaceutically acceptable salt thereof.

The present invention is also directed to compounds having the structure:

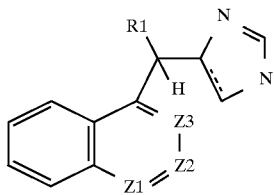

wherein each of Z1, Z2 and Z3 is N or $CR_2$, with the proviso that either one of Z1, Z2 or Z3 is N and the others of Z1, Z2 or Z3 are $CR_2$, or both Z1 and Z3 are N and Z2 is $CR_2$;

wherein $R_1$ is H; F; straight chained or branched $C_1$–$C_4$ alkyl, $C_1$–$C_4$ monofluoroalkyl or $C_1$–$C_4$ polyfluoroalkyl; straight chained or branched $C_1$–$C_4$ alkoxy, —OH; or —$(CH_2)_q OH$;

wherein each $R_2$ is independently H; F; Cl; Br; I; —$NO_2$; —CN; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —OH; —$(CH_2)_q OH$; —$COR_4$; $CO_2 R_4$; $CONHR_4$; phenyl; or benzyl;

wherein each $R_4$ is independently H; straight chained or branched $C_1$–$C_4$ alkyl, monofluoralkyl or polyfluoroalkyl; or phenyl; and wherein q is each independently 0, 1, 2 or 3;

or a pharmaceutically acceptable salt thereof

Furthermore, the compounds of the present invention are preferably at least 80% pure, more preferably at least 90% pure, and most preferably at least 95% pure. The invention further provides for the (+) or (–) enantiomer of any of the compounds described herein such as a cis isomer or trans isomer.

The compounds of the present invention may be present as enantiomers, disteriomers or isomers, or as a racemic mixture.

The present invention also includes tautomeric forms of compounds I; e.g., when X is N and R2 on the adjacent carbon atom is —OH, R2 may tautomerize with X to form a ketone at R2.

The present invention also encompasses compounds wherein two $R_3$s on different carbon atoms form a bridging ethylene or ethylene.

In an embodiment of the present invention Y is $CR_3 R_5$, and m+n is 3. In a further embodiment of the present invention Y is $CR_3 R_5$ and m+n is 2.

In a further embodiment of the present invention Y is $NR_6$. In another embodiment of the present invention X is N.

In an additional embodiment of the present invention two of Z1, Z2 and Z3 are $CR_2$ and the other is N.

In an embodiment of the present invention p is at least 1 and at least one $R_3$ is methyl. In a further embodiment of the present invention p is at least 1, at least one $R_3$ is methyl and X is N.

In another embodiment of the present invention at least one $R_2$ is methyl. In a further embodiment of the present invention $R_2$ is methyl and X is N.

In yet another embodiment of the present invention at least one $R_2$ is bromo. In a further embodiment of the present invention at least one R is bromo and X is N.

In an additional embodiment of the present invention at least one $R_2$ is methyl or phenyl. In yet another embodiment of the present invention $R_2$ is $C_1$–$C_3$ alkyl, $C_1$–$C_3$ alkoxy, or —OH.

In an embodiment of the present invention the compound has the structure:

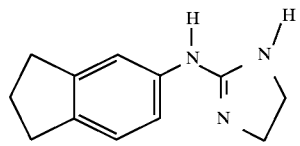

In a further embodiment of the present invention the compound has the structure:

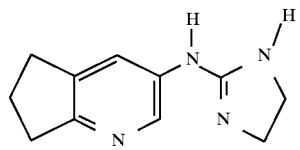

In an additional embodiment of the present invention the compound has the structure:

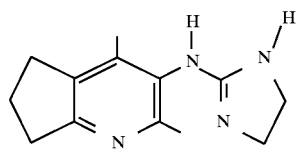

In a further embodiment of the present invention the compound has the structure:

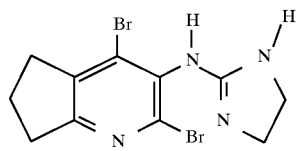

In an embodiment of the present invention the compound has the structure:

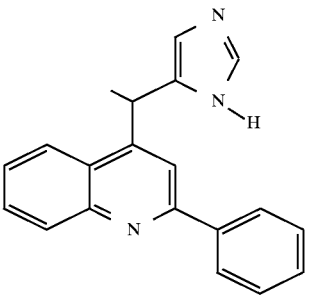

The present invention also provides a pharmaceutical composition comprising a therapeutically effective amount of the compounds described herein and a pharmaceutically acceptable carrier. In the present invention a "therapeutically effective amount" is any amount of a compound which, when administered to a subject suffering from a disorder against which the compound is effective, causes reduction, remission or regression of the disorder.

In one embodiment, the therapeutically effective amount is an amount from about 0.01 mg per subject per day to about 500 mg per subject per day, preferably from about 0.1 mg per subject per day to about 60 mg per subject per day, and most preferably from about 1 mg per subject per day to about 20 mg per subject per day. In the practice of this invention, the "pharmaceutically acceptable carrier" is any physiological carrier known to those of ordinary skill in the art useful in formulating pharmaceutical compositions.

The invention includes the pharmaceutically acceptable salts and complexes of all the compounds described herein. The salts include but are not limited to the following acids and bases. Examples of suitable inorganic acids include, but are not limited to, hydrochloric acid, hydrofluoric acid, hydrobromic acid, hydroiodic acid, sulfuric acid and boric acid. Examples of suitable organic acids include but are not limited to acetic acid, trifluoroacetic acid, formic acid, oxalic acid, malonic acid, succinic acid, tartaric acid, maleic acid, fumaric acid, oxalic acid, methanesulfonic acid, trifluoromethanesulfonic acid, benzoic acid, glycolic acid, lactic acid, citric acid and mandelic acid. Examples of suitable inorganic bases include, but are not limited to, ammonia, hydroxyethylamine are hydrazine. Examples of suitable organic bases include, but are not limited to, methylamine, ethylamine, trimethylamine, triethylamine, ethylenedlamine, hydroxiethylamine, morpholine, piperazine and guanidine. The invention further provides for the hydrates and polymorphs of all of the compounds described herein.

In one preferred embodiment, the pharmaceutical carrier may be a liquid and the pharmaceutical composition would be in the form of a solution. In another equally preferred embodiment, the pharmaceutically acceptable carrier is a solid and the pharmaceutical composition is in the form of a powder of tablet. In a further embodiment, the pharmaceutical carrier is a gel and the pharmaceutical composition is in the form of a suppository or cream. In a further embodiment, the compound may be formulated as part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for examples, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agent, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant, which are useful for intranasal administration.

Liquid pharmaceutical compositions which are sterile solutions or suspensions can be utilized for in, ramuscular, Intrathecal, intratracheal, epidural, intraperitoneal or subcutaneous injections. Sterile solutions an also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms such as pills, capsules, granules, tablets and powders, and liquid forms such as solutions, syrups, elixirs and suspensions. Forms useful for parenteral administration include sterile solutions, emulsions and suspensions.

Examples of suitable pharmaceutical carriers include any of the standard pharmaceutically accepted carriers known to those of ordinary skill in the art. Examples of such pharmaceutical carriers include, but are not limited to, phosphate buffered saline solution, water, emulsions such as oil/water emulsions or a triglyceride emulsion, various types of wetting agents, tablets, coated ablets and capsules. A suitable pharmaceutically acceptable carrier may be selected taking into account the chosen mode of administration.

Besides containing an effective amount of the compounds described herein the pharmaceutical compositions may also include suitable diluents, preservatives, solubilizers, emulsifiers, adjuvant and/or carriers.

The resulting pharmaceutical compositions may be liquids or lyophilized or otherwise dried formulations. Examples of suitable diluents include, but are not limited to, Tris-HCL, Tris-acetate and Tris-phosphate. The diluents employed may vary in their buffer content, pH and/or ionic strength. Examples of representative additives which may be used in the present invention include, but are not limited to, albumin or gelatin to prevent absorption to surfaces, detergents (e.g., Tween 20, Tween 80, Pluroric F68, bile acid salts), solubilizing agents (e.g., Thimeosal, benzyl alcohol), bulking substances or tonicity modifiers (e.g., lactose, mannitol), covalent attachment of polymers such as polyethylene glycol to the protein, complexation with metal ions, or incorporation of the material into or onto particulate preparation of polymeric compounds such as polylactic acid, polyglycolic acid, polyvinyl pyrrolidone, etc. or into liposomes, microemulsions, micelles, unilamellar or multimellar vesicles, erythrocyt ghosts, or spheroplasts. Such compositions will influence he physical state, solubility, stability, rate of in vivo elease, and rate of in vivo clearance of the compounds.

Examples of optional ingredients which may be included in the pharmaceutical compositions of the present invention include antioxidants, e.g., ascorbic acid; low molecular weight (less than about ten residues) polypeptides, i.e., polyarginine or tripeptide; proteins, such as serum albumin, gelatin, or immunoglobulins; amino acids, such as glycine, glutamine acid, aspartic acid, or arginine; chelating agents such as EDTA; and sugar alcohols such as mannitol or sorbitol.

The choice of composition will depend on the physical and chemical properties of the compounds. Controlled or sustained release compositions Include formulation of lipophilic depots (e.g., fatty acids, waxes, oils). Also comprehended by the invention are particulate compositions coated with polymers (e.g., poloxamers or polxamines) and compounds coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary nasal and oral.

Suitable topical formulations include gels, creams, solutions, emulsions, carbohydrate polymers, biodegradable matrices thereof; vapors, mists, a aerosols, or other inhalants. The compounds of the present invention may be encapsulated in a wafer, wax, film or solid carrier, including chewing gums. Permeation enhancers to aid in transport to movement across the epithelial layer are also known in the art and include, but are not limited to, dimethyl sulfoxide and glycols.

Optimal dosages to be administered may be determined by those skilled in the art, and will vary with the particular compound in use, the strength of the preparation, the mode of administration, and the advancement of he disease condition. Additional factors depending on the particular subject being treated, including subject age, weight, gender, diet, and time of administration, will result in a need to adjust dosages. Administration of the compound may be effected continuously or intermittently. One skilled in the art will readily appreciate that appropriate biological assays will be used to determine the therapeutic potential of the claimed compounds for treating $\alpha_2$-mediated disorders, in particular the disorders described herein.

The present invention also provides a method for treating an $\alpha_2$ adrenergic receptor associated disorder in a subject, which comprises administering to the subject an amount of a compound effective to treat the disorder, wherein the compound has the structure:

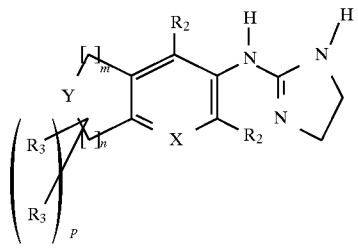

wherein X is $CR_7$; N; or $N^+O^-$;

wherein Y is O; CO; S; $CR_3R_5$; or $NR_6$;

wherein each $R_2$ is independently H; F; Cl; Br; I; $-NO_2$, $-CN$; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; $-OH$; $-(CH_2)_qOH$; $-COR_4$; $CO_2R_4$ ; $CONHR_4$; phenyl; or benzyl;

wherein each $R_3$ is independently H; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; $-(CH_2)_qOH$; $-OH$; $=N-OR_4$; $COR_4$; $CO_2R_4$; $CONHR_4$; phenyl; or benzyl;

wherein each $R_4$ is independently H; straight chained or branched $C_1$–$C_4$ alkyl, $C_1$–$C_4$ monofluoroalkyl or $C_1$–$C_4$ polyfluoroalkyl; or phenyl;

wherein each $R_5$ is independently H; straight chained or branched $C_1$–$C_4$ alkyl, $C_1$–$C_4$ monofluoroalkyl, or $C_1$–$C_4$ polyfluoroalkyl;

wherein $R_6$ is H; straight chained or branched $C_1$–$C_4$ alkyl; $C_1$–$C_4$; monofluoroalkyl or $C_1$–$C_4$ polyfluoroalkyl; straight chained or branched $C_1$–$C_4$ alkoxy; $-CH_2CH_2(CH_2)_qOH$; $COR_4$; $CO_2R_4$; $CONHR_4$; phenyl; or benzyl;

wherein each $R_7$ is independently H; $-CN$; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; $-OH$; $-(CH_2)_qOH$; $-COR_4$; $CO_2R_4$; $CONHR_4$; phenyl; or benzyl;

wherein m and n are each independently 0, 1, 2 or 3, provided that m+n is 2 or 3;

wherein each p is independently 0, 1 or 2; and wherein each q is independently 0, 1, 2 or 3;

or a pharmaceutically acceptable salt thereof.

The subject invention further provides a method for treating an $\alpha_2$ adrenergic receptor associated disorder in a subject, which comprises administering to the subject ar amount of a compound effective to treat the disorder, wherein the compound has the structure:

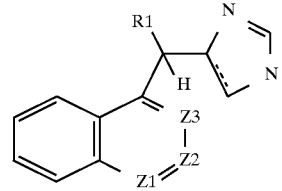

wherein each of Z1, Z2 and Z3 is N or $CR_2$, with the proviso that either one of Z1, Z2 or Z3 is N and the others of Z1, Z2 or Z3 are $CR_2$, or both Z1 and Z3 are N and Z2 is $CR_2$;

wherein $R_1$ is H; F; straight chained or branched $C_1$–$C_4$ alkyl, $C_1$–$C_4$ monofluoroalkyl or $C_1$–$C_4$ polyfluoroalkyl; straight chained or branched $C_1$–$C_4$ alkoxy, $-OH$; or $-(CH_2)_qOH$;

wherein each $R_2$ is independently H; F; Cl; Br; I; $-NO_2$, $-CN$; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; $-OH$; $-(CH_2)_qOH$; $-COR_4$; $CO_2R_4$; $CONHR_4$; phenyl; or benzyl;

wherein each $R_4$ is independently H; straight chained or branched $C_1$–$C_4$ alkyl, $C_1$–$C_4$ monofluoroalky or $C_1$–$C_4$ polyfluoroalkyl; or phenyl; and wherein q is each independently 0, 1, 2 or 3;

or a pharmaceutically acceptable salt thereof.

Examples of $\alpha_2$ adrenergic receptor associated disorders which may be treated in accordance with the subject invention include, but are not limited to, hypertension, pain, glaucoma, alcohol and drug withdrawal rheumatoid arthritis, ischemia, migraine, cognitive deficiency, spasticity, diarrhea and nasal congestion.

In a specific embodiment of the present invention the a adrenergic receptor associated disorder is migraine headache, hypertension or glaucoma.

13

The present invention also provides a method for treating pain in a subject, which comprises administering to the subject an amount of a compound effective to treat the subject's pain, wherein the compound has the structure:

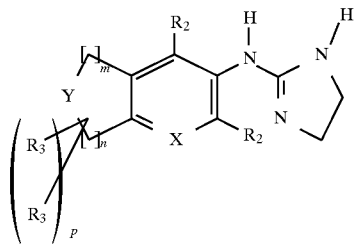

wherein X is $CR_7$; N; or $N^+O^-$;

wherein Y is O; CO; S; $CR_3R_5$; or $NR_6$;

wherein each $R_2$ is independently H; F; Cl; Br I; —$NO_2$, —CN; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —OH; —$(CH_2)_qOH$; —$COR_4$; $CO_2R_4$; $CONHR_4$; phenyl; or benzyl;

wherein each $R_3$ is independently H; straight: chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —$(CH_2)_qOH$; —OH; =N—$OR_4$; $COR_4$; $CO_2R_4$; $CONHR_4$; phenol; or benzyl;

wherein each $R_4$ is independently H; straight chained or branched $C_1$–$C_4$ alkyl, $C_1$–$C_4$ monofluoroalkyl or $C_1$–$C_4$ polyfluoroalkyl; or phenyl;

wherein each $R_5$ is independently H; straight chained or branched $C_1$–$C_4$ alkyl, $C_1$–$C_4$ monofluoroalkyl, or $C_1$–$C_4$ polyfluoroalkyl;

wherein $R_6$ is H; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —$CH_2CH_2(CH_2)_qOH$ $COR_4$; $CO_2R_4$; $CONHR_4$; phenyl; or benzyl;

wherein each $R_7$ is independently H; —CN; straight chained or branched $C_1$–$C_4$ alkyl; $C_1$–$C_4$ monofluoroalkyl or $C_1$–$C_4$ polyfluoroalkyl; straight chained or branched $C_1$–$C_4$ alkoxy; —OH; —$(CH_2)_qOH$; —$COR_4$; $CO_2R_4$; $CONHR_4$; phenyl; or benzyl;

wherein m and n are each independently 0, 1, 2 or 3, provided that m+n is 2 or 3;

wherein each p is independently 0, 1 or 2; and wherein each q is independently 0, 1, 2 or 3;

or a pharmaceutically acceptable salt thereof 078665795

The present invention also provides a method or treating pain in a subject, which comprises administering to the subject an amount of a compound effective to treat the subject's pain, wherein the compound has the structure:

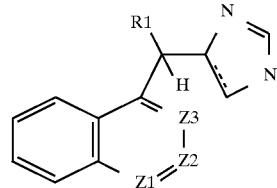

wherein each of Z1, Z2 and Z3 is N or $CR_2$, with the proviso that either one of Z1, Z2 or Z3 is N and the

14 others of Z1, Z2 or Z3 are $CR_2$, or both Z1 and Z3 are N and Z2 is $CR_2$;

wherein $R_1$ is H; F; straight chained or branches $C_1$–$C_4$ alkyl, $C_1$–$C_4$, monofluoroalkyl or $C_1$–$C_4$ polyfluoroalkyl; straight chained or branched $C_1$–$C_4$ alkoxy, —OH; or —$(CH_2)_qOH$;

wherein each $R_1$ is independently H; F; Cl; Br; I; —$NO_2$, —CN; straight chained or branched $C_1$–$C_4$ akyl; $C_1$–$C_4$ monofluoroalkyl or $C_1$–$C_4$ polyfluoroalkyl; straight chained or branched $C_1$–$C_4$ alkoxy; —OH; —$(CH_2)_qOH$; —$COR_4$; $CO_2R_4$; $CONHR_4$; phenyl; or benzyl;

wherein each $R_4$ is independently H; straight: chained or branched $C_1$–$C_4$ alkyl, $C_1$–$C_4$, monofluoroalkyl or $C_1$–$C_4$ polyfluoroalkyl; or phenyl; and wherein q is each independently 0, 1, 2 or 3;

or a pharmaceutically acceptable salt thereof.

This invention will be better understood from the Experimental Details which follow. However, ore skilled in the art will readily appreciate that the specific methods and results discussed are merely illustrative of the invention as described more fully in the claims which follow thereafter.

EXPERIMENTAL DETAILS

The compounds of Examples 1–31 may be obtain d using the methods depicted in Schemes 1–4, except for example 2 which was obtained by bromination of example 1, and for examples 27 and 28 which were prepared from example 21 by hydrogen peroxide oxidation and by bromination, respectively. Only one amine, 5-aminoindan, was commercially available and was used to prepare example 1. Upon bromination, 5-aminoindan provided the amine precursor to example 3. The other amines were obtained from the corresponding nitro compounds by hydrogenation or tin(II) chloride reduction (Scheme 1). All of the nitropyridines were synthesized by the reaction of a ketone with 1-methyl-3,5-dinitro-2-pyridone which was in turn obtained from 1-methyl-2-pyridone by nitration (Scheme 2). The other nitro compounds were either commercially available or obtained from functionalization of commercially available nitro compounds as illustrated in Scheme 3. Exceptions include example 11 whereby the nitro group was generated by nitration. The synthesis of examples 29–31 is depicted in Scheme 4.

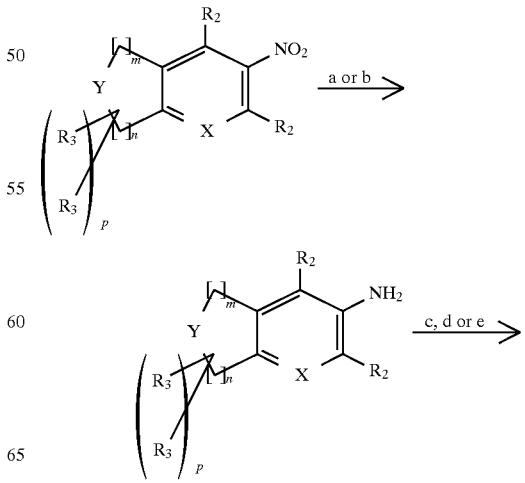

Scheme 1

-continued
Scheme 1

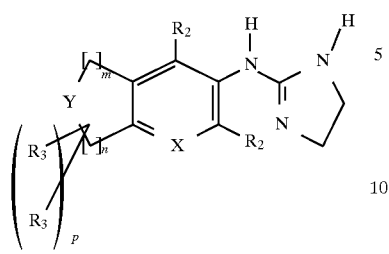

Scheme 2

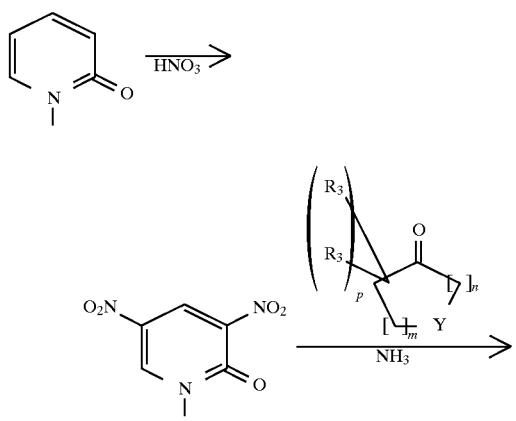

Scheme 3

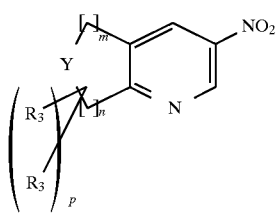

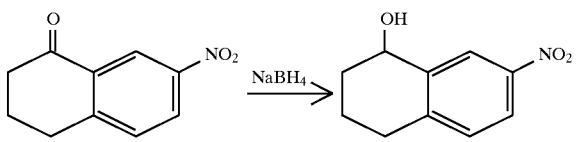

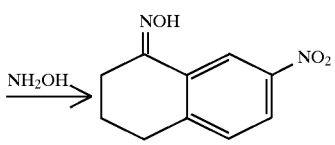

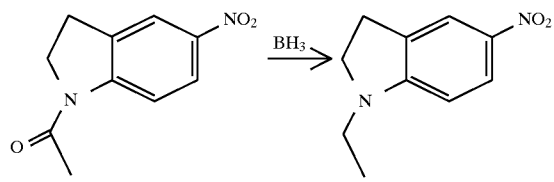

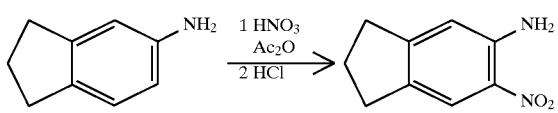

-continued
Scheme 3

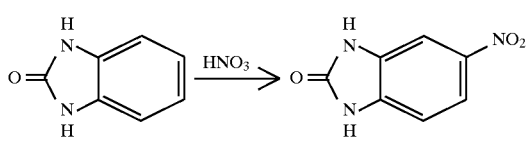

Scheme 4

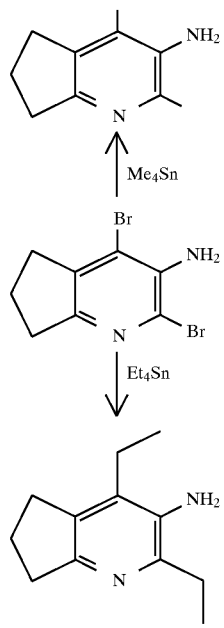

The compounds of Examples 32–44 may be obtained using the methods depicted in Schemes 5 and 6. Example 32–38 were prepared using the general scheme shown in Scheme 5, and Examples 39–44 were prepared according to Scheie 6.

Abbreviations in Schemes 5 and 6:

| | |
|---|---|
| n-BuLi | n-butyl lithium |
| DMF | dimethylformamide |
| LDA | lithium diisopropyl amide |
| Me | methyl |
| Et | ethyl |
| Ph | phenyl |
| RT | room temperature |
| DMSO | dimethyl sulfoxide |
| AcCl | acetyl chloride |
| Py | pyridine |
| THF | tetrahydrofuran |
| TBDMS | t-butyl dimethylsilyl |

Scheme 5

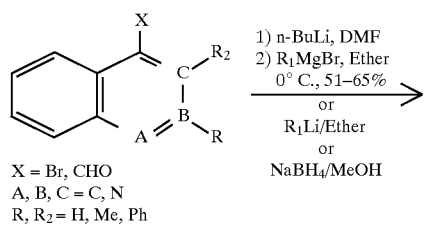

1) n-BuLi, DMF
2) R$_1$MgBr, Ether
0° C., 51–65%
or
R$_1$Li/Ether
or
NaBH$_4$/MeOH X = Br, CHO
A, B, C = C, N
R, R$_2$ = H, Me, Ph

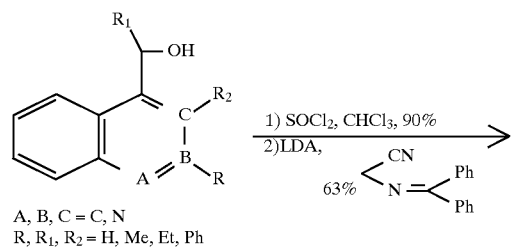

1) SOCl$_2$, CHCl$_3$, 90%
2) LDA, 
$\underset{63\%}{\text{CN}\diagup\text{C(=NPh)Ph}}$ A, B, C = C, N
R, R$_1$, R$_2$ = H, Me, Et, Ph

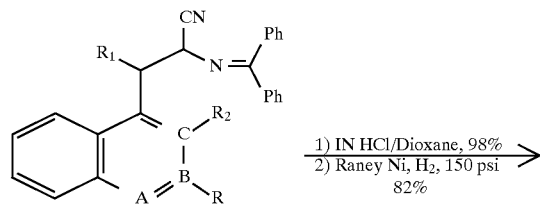

1) 1N HCl/Dioxane, 98%
2) Raney Ni, H$_2$, 150 psi
82%

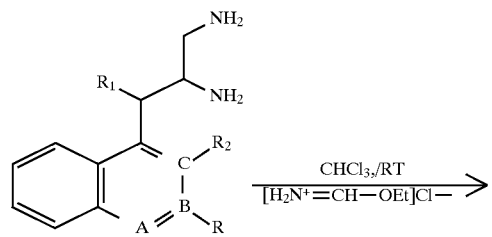

CHCl$_3$/RT
[H$_2$N$^+$=CH—OEt]Cl$^-$

-continued
Scheme 5

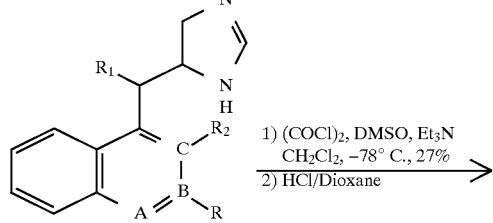

1) (COCl)$_2$, DMSO, Et$_3$N
   CH$_2$Cl$_2$, −78° C., 27%
2) HCl/Dioxane

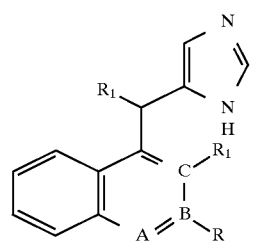

2 HCl

Scheme 6

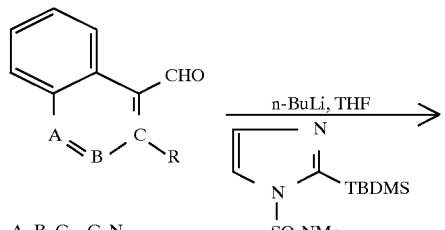

n-BuLi, THF

[imidazole with TBDMS and SO$_2$NMr$_3$]

A, B, C = C, N
R = H, CH$_3$

-continued
Scheme 6

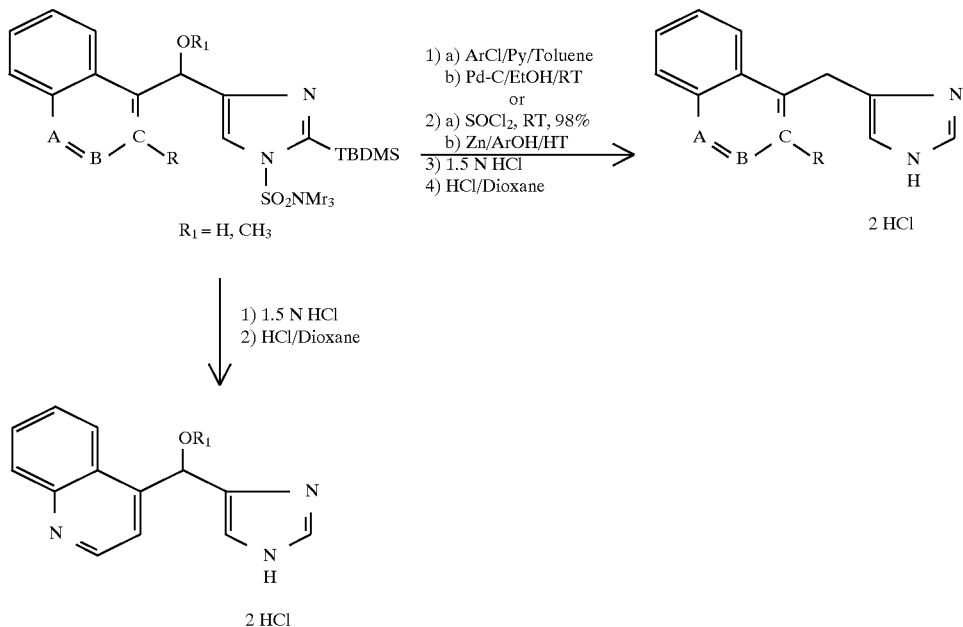

$R_1$ = H, $CH_3$

Example 1

2-(5-Indanylamino)-2-imidazoline

A mixture of 5-aminoindan (200 mg, 1.50 mmol) and 2-imidazolinesulfonic acid (450 mg, 3.00 mmol) in isobutyl alcohol (5 mL) was heated at reflux for 3 h and then stirred overnight. The solvent was removed to give a dark oil. It was flash chromatographed over silica gel (EtOAc:MeOH:Et$_3$N= 6:2:1) to afford a yellow solid. The solid was redissolved in dichloromethane, and washed with saturated aqueous Na$_2$CO$_3$. The organic layer was cried and concentrated to give yellow crystals (220 mg, 73% yield): mp 41°–42° C.; EIMS m/z=201 (M$^+$). Anal. Calcd. for $C_{12}H_{15}N_3$4/5H$_2$O: C, 66.82; H, 7.74; N, 19.48. Found: C, 6.77; H, 7.31; N, 19.24.

Example 2

2-(6-Bromo-5-indanylamino)-2-imidazoline hydrobromide

To a solution of 2-(5-Indanylamino)-2-imidazoline (100 mg, 0.497 mmol) in acetic acid (7 mL) was added a solution of bromine (153 mg, 0.957 mmol) in acetic acid 1 mL). The resulting mixture was stirred for 5 min, and the solvent was removed. The residue was flash chromatographec over silica gel (EtOAc:MeOH:Et$_3$N=6:2:1) to afford a solid, which was recrystallized from dichloromethane/hexane to give a beige solid (25 mg, 14% yield): mp 220°–221° C.; HRMS (EI) calcd. for $C_{12}H_{14}N_3$Br 279.0371, obsd. 279.0383. Anal. Calcd. for $C_{12}H_{14}N_3$Br.HBr.2/3H$_2$O: C, 38.63; H, 4.41; N, 11.26; Br, 42.83. Found: C, 39.10; H, 4.21; N, 10.87; Br, 42.37.

Example 3

2-(4,6-Dibromo-5-indanylamino)-2-imidazoline 4,6-Dibrormo-5-arninoindane. To a solution of 5-aminoindane (1.00 g, 7.51 mmol) in acetic acid (40 mL) was , added bromine (3 mL). The resulting mixture was stirred for an hour and then concentrated by half. Chloroform was added to give a precipitate. The solid was isolated, and washed with chloroform to afford a lightly tinted solid (2.06 g, 94% yield): mp 220°–221° C.; $^1$H NMR (300 MHz, CD$_3$OD) d 2.07 (m, 2H), 2.90 (m, 4H), 7.33 (s, 1H).

3-Acetyl-2-(4,6-dibromo-5-indanylamino)-2-imidizolinone. A mixture of the above solid (200 mg, 0.687 mmol) and N-acetyl-2-imidazolidone (106 mg, 0.827 mmol) in phosphorus oxychloride (5 mL) was stirred at 50° C. for 48 h. The solvent was removed. The residue was dissolved in dichloromethane (5 mL) and washed with 1N queous NaOH solution (2×5 mL). The organic layer was dryed (Na$_2$SO$_4$), filtered and concentrated to give a white solid (270 mg, 99%). This solid (220 mg, 0.548 mmol) was heated in water (5 mL) at reflux for 4 h, and then cooled to room temperature. The resulting solution was washed with CH$_2$Cl$_2$, and basined with 1N aqueous NaOH until pH=8. The aqueous layer was then extracted with EtOAc (2×10 mL), and the combined extracts were dried and concentrated to yield a white solid (91 mg, 46% yield): mp 163°–164° C.; CIMS m/e=360 (MH$^+$); Anal. Calcd. for $C_{12}H_{14}N_3$Br$_2$: C, 40.14; H, 3.65, N; 11.70; Br, 44.51,. Found: C, 40.42; H, 3.95; N, 11.41; Br, 44.54.

Example 4

2-(1,2,3,4-Tetrahydro-1-oxo-naphth-7-yl)amino-2-imidazoline

7-Amino-1-tetralone. A suspension of 7-nitro-1-tetralone (2.00 g, 10.5 mmol) in MeOH (20 mL) was treated with 10% Pd-C (100 mg) and hydrogenated at 1 atm for 5 h. Filtration through Celite gave a brown solid (1.38 9 g. It was suspended in CHCl$_3$ and flash chromatographed over silica gel (69 g) eluting with EtOAc/hexane (1:2) to afford a tan solid (0.62 g, 37% yield): mp 137°–138° C.

2-(1,2,3,4-Tetrahydro-1-oxo-naphth-7-yl)amino-2 imidazoline. The above solid (150 mg, 0.93 mmol) was suspended in isobutyl alcohol (5 mL), treated with 2-imidazoline sulfonic acid (280 mg, 1.86 mmol) and heated at reflux overnight. More 2-imidazoline sulfonic acid (70 mg) was added and reflux was continued overnight. The solvent was evaporated off to give a brown oil. It was dissolved in $CHCl_3$-MeOH and flash chromatographed over silica gel (17 g) eluting with $EtOAc/MeOH/Et_3N$ (10:2:1) to afford a pale yellow foam (157 mg, 74% yield). A portion (151 mg) was dissolved in EtOH and treated with fumaric acid (39 mg) in EtOH to give some off-white crystals (100 mg): mp 198°–201° C. (dec.); CIMS, h m/e=230 (MH$^+$). Anal. Calcd. for $C_{13}H_{15}N_3O\ C_4H_4O_4$: C, 59.12; H, 5.55; N, 12.17. Found: C, 58.91; H, 5.50; N, 12.03.

Example 5

2-(8-Bromo-1,2,3,4-Tetrahydro-1-oxo-naphth-7-yl) amino-2-imidazoline

7-Amino-8-bromo-1-tetralone. 7-Amino-1-tetralone (457 mg, 2.83 mmol) was dissolved in acetic acid (8 mL) and treated with bromine (150 mL, 2.91 mmol) dropwise. After 10 min., more bromine (17 mL) was added. Then the solvent was evaporated off to give a light brown solid. It was partitioned between $Na_2CO_3$ solution and EtOAc From the organic phase was obtained a semi-solid (696 mg). It was dissolved in $CHCl_3$ and flash chromatographed over silica gel 50 g) eluting with EtOAc/hexane (1:4) to afford a yellow solid (320 mg, 470 yield): mp 93°–96° C.

2-(8-Bromo-1,2,3,4-Tetrahydro-1-oxo-naphth-7 yl)amino-2-imidazoline. The above solid (100 mg, 0.42 mmol) was added to a mixture of 1-acetyl-2-imidazolidone (63 mg, 0.49 mmol) and $POCl_3$ (3 mL). The mixture was heated at 50°–60° C. overnight. Then the solvent was evaporated off. The residue was dissolved in $CH_2Cl_2$ (8 mL) and washed with 1N NaOH twice. The organic layer was dried ($MgSO_4$), filtered and concentrated to give an off-white foam (123 mg). It was heated at reflux in water (5 mL) for 2.5 h. The cooled mixture was filtered and the filtrate was basined with NaOH and $Na_2CO_3$ solutions to give a yellow solid (47 mg, 37% yield) which was filtered off and washed with water. It was dissolved in MeOH and treated with fumaric acid (17 mg) in MeOH. Then the solvent was evaporated off. The residue was triturated with MeOH to afford brown crystals (35 mg): mp 204°–207° C. (dec.); CIMS, m/e=308, 310 (MH$^+$). Anal. Calcd. for $C_{13}H_{14}BrN_3O.C_4H_4O_4$: C, 48.13; H, 4.28; N. 9.90. Found: C, 48.37; H, 4.27; N, 9.82.

Example 6

2-(1,2,3,4-Tetrahydro-1-hydroxy-naphth-7-yl)amino-2-imidazoline

1-Hydroxy-7-nitro-tetralln. A suspension of 7-nitro-1-tetralone (2.00 g, 10.5 mmol) in EtOH (15 mL) was cooled by an ice water bath and treated with $NaBH_4$ (0.40 g, 10.6 mmol). The mixture was stirred at room temperature for 2 h and then poured into ice water (50 mL) and extracted with EtOAc (3×20 mL). The extract was washec with NaCl solution, dried ($MgSO_4$), filtered and concentrated to give a white solid (1.92 g, 95% yield).

7-Amino-1-hydroxy-tetralin. The above solid (0.92 g, 4.76 mmol) was dissolved in dry MeOH (10 mL), treated with 10% Pd-C (100 mg) and hydrogenated at 1 atm for 4 h. The mixture was filtered through Celite to give an orange solid (0.777 g). It was dissolved in $CHCl_3$ and flash chromatographed over silica gel (42 g) eluting with EtOAc/hexane (1:2 and then 1:1) to afford a pinkish solid (691 mg, 89% yield).

2-(1,2,3,4-Tetrahydro-1-hydroxy-naphth-7yl)amino-2-imidazoline. The above amine (200 mg, 1.23 mmol) was mixed with 2-imidazolinesulfonic acid (368 mg, 2.45 mmol) in isobutyl alcohol (6 mL) and heated at reflux overnight. The solvent was removed, and the residue was dissolved in $EtOAc/MeOH/Et_3N$ (5:5:1) and flash chromatographed over silica gel (18 g) eluting with the same solvent to give a white foam (225 mg, 79% yield). It was dissol ed in EtOH and treated with fumaric acid (113 mg) in EtOH. Upon dilution with EtOAc and standing at −15° C., the solution give a white solid (241 mg): mp 180°–182° C. (dec.). Anal. Calcd. for $C_{13}H_{17}N_3O.C_4H_4O_4$: C, 58.78; H, 6.09; N, 12.10. Found: C, 58.98; H, 6.39; N, 11.93.

Example 7

2-(1,2,3,4-Tetrahydro-1-methyl-naphth-7-yl)amino-2-imidazoline

1-Methylene-7-nitro-tetralin. 7-Nitro-1-tetralone (1.00 g, 5.23 mmol) was dissolved in dry THF (5 mL) and added to a solution of methyltriphenylphosphonium bromide (2.00 g, 5.60 mmol) and n-butyllithlum (2.5M in hexanes, 2.2 mL, 5.5 mmol) in THF (10 mL) cooled by an ice water bath. The mixture was allowed to warm to room temperature and stirred overnight. It was poured into ice water 45 mL) and extracted with EtOAc (3×20 mL). The extract was washed with NaCl solution, dried ($MgSO_4$), filtered and concentrated to give a black solid (1.504 g). It was dissolved in $CHCl_3$ and flash chromatographed over silica gel (65 g) eluting with EtOAc/hexane (1:20) to afford a white solid (263 mg, 27% yield): mp 45°–470° C.

2-(1,2,3, 4-Tetrahydro-1-methyl-naphth-7yl)amino-2-imidazoline. The above solid was dissolved ir dry MeOH (5 mL), treated with 10% Pd-C (50 mg) and hydrogenated at 1 atm for 4 h. The mixture was then filtered through Celite to afford a light orange oil (211 mg). It was mixed with 2-imidazolinesulfonic acid (393 mg, 2.62 mmol) in isobutyl alcohol (6 mL) and heated at reflux overnight. The solvent was removed to give a light blue oil which was dissolved in $CHCl_3$ and flash chromatographed over silica gel (30 g) eluting with $EtOAc/MeOH/Et_3N$ (5:2:0.7) to give a white foam (177 mg, 56% yield). It was dissolved in EtOH and treated with fumaric acid (89 mg) in EtOH. Upon refrigeration, the solution afforded a white solid (202 mg): mp 185°–187° C. (dec.); CIMS m/e=230 (MH$^+$). Anal. calcd. for $C_{14}H_{19}N_3.C_4H_4O_4.1/10H_2O$: C, 62.27; H, 6.73; N, 12.10 Found: C, 62.15; H, 6.65; N, 11.81.

Example 8

2-(1,2,3,4-Tetrahydro-1-methoxyimin)-naphth-7-yl) amino-2-imidazoline

1-Methoxyimino-7-nitro-tetralin. 7-Nitro-tetralone (1.00 g, 5.23 mmol) was suspended in EtOH (10 mL), cooled by an ice water bath and treated with methoxylamine hydrochloride (0.52 g, 6.23 mmol) and sodium bicarbonate (0.57 g, 6.78 mmol). The mixture was stirred at room temperature for 1 h before ice water (50 mL) was added. A precipitate formed which was filtered off to give a white solid 1.10 g, 95% yield). This solid contained two geometric isomers in a ratio of 7:1. It was dissolved in $CCl_4/CHCl_3$ and flash chromatographed over silica gel (50 g) eluting with EtOAc/hexane (1:20) to afford the major isomer as a white solid. It was recrystallized from hot EtOAc to give colorless crystals (556 mg): mp 128°–131° C.

7-Amino-1-Methoxyimino-tetralin. 1-Methoxyimino-7-nitro-tetralin (252 mg, 1.14 mmol, was treated with 10%

Pd-C (25 mg) in MeOH (5 mL) and hydrogenated at 1 atm for 2 h. The mixture was filtered through Celite to give a yellowish solid (208 mg, 96% yield).

2-(1,2,3,4-Tetrhydro-7-methoxyimino-naphth-7-yl)amino-2-imidazoline. The above solid (206 mg, 1.08 mmol) was mixed with 2-imidazolinesulfonic acid (325 mg, 2.16 mmol) in isobutyl alcohol (7 mL) and heated at reflux for two days. The solvent was removed and the residue was dissolved in $CHCl_3$ and flash chromatographed over silica gel (18 g) eluting with $EtOAc/MeOH/Et_3N$ (10:2:0.6) to give a white foam (250 mg, 89% yield). It was dissolved in EtOH ind treated with fumaric acid (113 mg) in EtOH. Upon refrigeration, the solution afforded a white solid (152 mg): mp 201°–202° C. (dec.) Anal. Calcd. for $C_{14}H_{18}N_4O \cdot C_4H_4O_4$: C, 57.75; H, 5.92; N, 14.96. Found: C, 57.54; H, 5.79; N, 14.68.

Example 9

2-(1-Acetyl-indolin-5-yl)amino-2-imidizoline

1-Acetyl-5-nitroindoline (1.87 g, 9.07 mmol) was suspended in dry MeOH (40 mL), treated with 10% Pd-C (157 mg) and hydrogenated at 1 atm for 5 h. The mixture wis filtered through Celite to give a light brown solid (1.33 g, 83 g yield). A portion (207 mg, 1.17 mmol) was mixed with 2-imidazolinesulfonic acid (349 mg, 2.32 mmol) in isobutyl alcohol (8 mL) and heated at reflux for 2 days. Evaporation of the solvent gave a light brown oil which was dissolved in $EtOAc/MeOH/Et_3N$ (25:15:2) and flash chromatographed over silica gel (15 g) eluting with the same solvent to afford a light brown foam. It was again dissolved in $EtOAc/MeOH/Et_3N$ (10:2:0.6) and flash chromatographed over silica gel eluting with the same solvent to give a yellow solid 82 mg, 29% yield). It was dissolved in MeOH/EtOH and treated with fumaric acid (38 mg) in EtOH to afford light brown crystals (67 mg): mp 200°–203° C. (dec.). Anal. Calcd. for $C_{13}H_{16}N_4O \cdot C_4H_4O_4$: C, 56.66; H, 5.59; N, 15.55. Found: C, 56.39; H, 5.40; N, 15.38.

Example 10

2-(1-Ethyl-indolin-5-yl)amino-2-imidazoline

1-Ethyl-5-nitro-indoline. 1-Acetyl-5-nitro-indoline (1.00 g, 4.85 mmol) was added to borane-THF complex 1M, 10 mL, 10 mmol). The mixture was heated at reflux for 4 h. With ice-water bath cooling, the mixture was slowly reated with 6N HCl (4 mL). Then the mixture was heated at 50° C. for 1 h. The organic solvent was evaporated off and the resulting suspension was filtered to give an orange solid (1.02 g) which was washed with water: mp 97°–98° C.

2-(1-Ethyl-indolin-5-yl)amino-2-imidazoline. The above solid (400 mg, 2.08 mmol) was suspended in MEDH (8 mL), treated with 10% Pd-C (40 mg) and hydrogenated at 1 atm for 2 h. The mixture was filtered through Celite to give an oil (270 mg). It was mixed with 2-imidazolinesulfonic acid (500 mg, 3.33 mmol) in isobutyl alcohol (8 mL) are heated at reflux overnight. The solvent was removed to give a dark oil. It was dissolved in $CHCl_3$ and flash chromatographed over silica gel (15 g) eluting with $EtOAc/MeOH/Et_3N$ (20:4:1) to give a dark foam (157 mg). It was dissolved in EtOH and treated with fumaric acid (79 mg) in EtOH to give, upon refrigeration, an orange solid (137 mg, 19% yield): mp 198°–200° C. (dec.). Anal. Calcd. for $C_{13}H_{18}N_4 \cdot C_4H_4O_4$: C, 58.95; H, 6.40; N, 16.17. Found: C, 58.83; H, 6.39; N, 16.03.

Example 11

2-(6-Nitro-indan-5-yl)amino-2-imidazoline

5-Acetamido-6-nitro-indan. 5-Amino-indan (3.00 g, 22.53 mmol) was added slowly to acetic anhydride (10 mL) cooled by an ice water bath. After 15 min., 70% $HNO_3$ (3 mL, 46.99 mmol) was carefully added dropwise so that the temperature remained below 26° C. The mixture was allowed to slowly warm to room temperature and stirred for 2 days. It was then treated with ice water (60 mL) and extracted with EtOAc (3×20 mL). The extract was washed with water, $Na_2CO_3$ solution, dried ($MgSO_4$), filtered and concentrated to give a dark oil (3.51 g). It was dissolved in $CHCl_3$ and flash chromatographed over silica gel (180 g) eluting with EtOAc/hexane (1:10) to afford a yellowish orange solid (1.43 g, 29% yield): mp 100°–104° C.

5-Amino-6-nitro-indan. The above solid (203 mg, 0.92 mmol) was heated at reflux in 4N HCl (4 mL) for 6 h. The mixture was basined with $Na_2CO_3$ solution and extracted with EtOAc (3×4 mL) to give an orange solid (156 mg, 95% yield).

2-(6-Nitro-indan-5-yl)amino-2-imidazoline. The above solid (153 mg, 0.86 mmol) was dissolved in $CHCl_3$ (3 mL), cooled by an ice water bath, and treated with thiophosgene (80 mL, 1.05 mmol) and then $NaHCO_3$ (220 mg, 2.62 mmol) in water (3 mL). The mixture was stirred at room temperature for 6 h before more thiophosgene (80 mL) and $NaHCO_3$ (220 mg) were added. The mixture was stirred overnight and then extracted with $CHCl_3$ (2×4 mL) to give an orange oil (172 mg, 91% yield). It was suspended in MeOH (5 mL) and treated with ethylenediamine (250 mL, 3.74 mmol). The mixture was heated at reflux for 5 h before the solvent was evaporated off to give a dark oil. It was suspended in $CHCl_3$ and flash chromatographed over silica gel (17 g) eluting with $EtOAc/hexane/Et_3N$ (15:5:1) to afford an orange solid (130° C. mg, 68% yield). A portion (64 mg) was dissolved in EtOH and treated with fumaric acid (30 mg) in EtOH to give a yellow solid (57 mg): mp 213°–214° C. (dec.). Anal. Calcd. for $C_{12}H_{14}N_4O_2 \cdot 3/4 C_4H_4O_4 \cdot 1/2 H_2O$: C, 52.63; H, 5.30; N, 16 37. Found: C, 52.51; H, 5.11; N, 16.16.

Example 12

2-(5,6,7,8-Tetrahydro-6-methyl-quinolin-3-yl)amino-2-imidazoline

1-Methyl-3,5-dinitro-2-pyridone. To a mixture of 1-methyl-2-pyridone (16.3 g, 0.15 mmol and sulfuric acid (150 mL being heated at 100° C. was added nitric acid (57 mL) in portions of 1–2 mL. The temperature during the addition of the acid was kept at 95°–110° C. The reaction mixture was then heated at 100° C. for 16 h, during which time considerable amounts of brown fumes were evolved. The reaction mixture was then allowed to cool to room temperature and was poured into ice water (600 mL). The product (8.2 g, 28 yield) was filtered off and washed with water until free of acids.

5,6,7,8-Tetrahydro-6-methyl-3-nitro-quinoline. 4-Methylcyclohexanone (170 mg, 1.52 mmol) was mixed with 1-methyl-3,5-dinitro-2-pyridone (300 mg, 1.51 mmol) in 1M methanolic ammonia (30 mL, 30 mmol). The solution was heated at gentle reflux for 3 h. Evaporation of the solvent gave an orange residue which was suspended in $CHCl_3$ and flash chromatographed over silica gel (16 g) eluting with EtOAc/hexane (1:10) to afford a white solid (211 mg, 73% yield): mp 50°–52° C.

3-Amino-5,6,7,8-tetrahydro-6-methylquinoline. The above solid (211 mg, 1.10 mmol) was dissolved in MEOH (4 mL), treated with 10% Pd-C (20 mg) and hydrogenated Ct 1 atm for 3 h. Filtration through Celite gave a sticky white solid (176 mg, 99% yield).

2-(5,6,7,8-Tetrahydro-6-methyl-quinolin-3-yl)amino-2-imidazoline. The above solid (174 mg, 1.07 mmol) was mixed with 2-imidazolinesulfonic acid (322 mg, 2.14 mmol) in isobutyl alcohol (5 mL) and heated at reflux for 2.5 days. The solvent was evaporated off to give a reside which was dissolved in CHCl$_3$ and flash chromatographed over silica gel (19 g) eluting with EtOAc/MeOH/Et$_3$N (20:3:1) to afford an off-white solid (247 mg, 100% yield). It was dissolved in EtOH and treated with fumaric acid (125 mg) in EtOH. Upon refrigeration, the solution gave a white solid (98 mg): mp 192°–195° C. (dec.). Anal. Calcd. for C$_{13}$H$_{18}$N$_4$.1.4C$_4$H$_4$O$_4$: C, 56.87; H, 6.06; N, 14.26. Found: C, 56.77; H, 6.00; N, 14.55.

Example 13

2-(5,6,7,8-Tetrahydro-7-methyl-quinolin-3-yl)amino-2-imidazoline 5,6,7,8-Tetrahydro-7-methyl-3-nitro-quinoline. 3-Methylcyclohexanone (0.56 g, 4.99 mmol) was mixed with 1-methyl-3,5-dinitro-2-pyridone (1.00 g, 5.02 mmol) in 1M methanolic ammonia (50 mL, 50 mmol) and heated at reflux overnight. The solvent was evaporated off and the residue was suspended in CHCl$_3$ and flash chromatographed over silica gel (43 g) eluting with EtOAc/hexane (1:10) to afford a white solid (515 mg, 63% yield): mp 55°–56° C.

3-Amino-5,6,7,8-tetrahydro-7-methylquinoline. The above solid (245 mg, 1.51 mmol) was dissolved in MeOH (5 mL), treated with 10% Pd-C (27 mg) and hydrogenated at 1 atm for 2 h. Filtration through Celite gave a colorless oil (212 mg).

2-(5,6,7,8-Tetrahydro-7-methyl-quinolin-3-yl)amino-2-imidazoline. The above amine (208 mg, 1.57 mmol) was mixed with 2-imidazolinesulfonic acid (470 mg, 3.13 mmol) in isobutyl alcohol (7 mL) and heated at reflux for 2 days. The solvent was evaporated off to give a residue which was dissolved in CHCl$_3$ and flash chromatographed over silica gel (19 g) eluting with EtOAc/MeOH/Et$_3$N (20:3:1) to afford a white solid (289 mg, 92% yield). A portion 135 mg) was dissolved in EtOH and treated with fumaric acic (157 mg) in EtOH to give white crystals (162 mg): mp 197°–198° C. (dec.). Anal. Calcd. for C$_{13}$H$_{18}$N$_4$.2C$_{13}$H$_4$O$_4$:C, 54.54; H, 5.67; N, 12.12. Found: C, 54.25; H, 5.86; N, 11.91.

Example 14

2-(5,6,7,B-Tetrahydro-8-methyl-quinolin-3-yl)amino-2-imidazoline 5,6,7,8-Tetrahydro-8-methyl-3-nitro-quinoline. 2-Methylcyclohexanone (170 mg, 1.52 mmol) was mixed with 1-methyl-3,5-dinitro-2-pyridone (296 mg, 1.49 mmol) in 1M methanolic ammonia (30 mL, 30 mmol) and heated at reflux for 3 h. The solvent was evaporated off and the residue was suspended in CHCl$_3$ and flash chromatographed over silica gel (19 g) eluting with EtOAc/hexane (1:10) to afford a white solid (213 mg, 75% yield): mp 61°–63° C.

3-Amino-5,6,7,8-tetrahydro-8-methylquinoline. The above solid (211 mg, 1.10 mmol) was dissolved in MEOH (4 mL), treated with 10% Pd-C (20 mg) and hydrogenated at 1 atm for 3 h. Filtration through Celite gave a colorless oil (180 mg, 101% yield).

2-(5,6,7,8-Tetrahydro-8-methyl-quinolin-3-yl)amino-2-imidazoline. The above amine (178 mg, 1.10 mmol) was mixed with 2-imidazolinesulfonic acid (322 mg, 2.14 mmol) in isobutyl alcohol (5 mL) and heated at reflux for 2.5 days. The solvent was evaporated off to give a residue which was dissolved in CHCl$_3$ and flash chromarographed over silica gel (18 g) eluting with EtOAc/MeOH/Et$_3$N (20:3:1) to afford a pale brown foam (206 mg, 82% yield). It was dissolved in EtOH and treated with fumaric acid (208 mg) in EtOH. Upon refrigeration, the solution gave a white solid (135 mg): mp 155°–160° C. (dec.). Anal. Calcd. for C$_{13}$H$_{18}$N$_4$.1.75C$_4$H$_4$O$_4$: C, 55.42; H, 5.81; N, 12.93. Found: C, 55.44; H, 5.88; N, 13.03.

Example 15

(5R),(8S)-2-(5,6,7,8-Tetrahydro-8-isopropyl-5-methyl-quinolin-3-yl)amino-2-imidazoline (5R), (8S)-3-Amino-5,6,7,8-tetrahydro-8-isopropyl-5-methylquinoline. (−)-Menthone (390 mg, 2.53 mm(1) was mixed with 1-methyl-3,5-dinitro-2-pyridone (500 mg, 2.51 mmol) in 1M methanolic ammonia (50 mL, 50 mmol) and heated at reflux overnight. The solvent was evaporated off and the residue was dissolved in CHCl$_3$ and flash chromatographed over silica gel (37 g) eluting with EtOAc/hexane (1:20) to afford a colorless oil (248 mg, 1.06 mmol). It was dissolved in MeOH (5 mL), treated with 10% Pd-C (27 mg) and hydrogenated at 1 atm for 2 h. Filtration through Celite gave a pale yellow solid (207 mg). It was partitioned between CH$_2$Cl$_2$ and 2N HCl. The organic layer was further extracted with 2N HCl before the aqueous layer was basined with Na$_2$CO$_3$ solution and extracted with CH$_2$Cl$_2$ to afford a white solid (123 mg, 24% yield).

(5R), (8S)-2-(5,6,7,8-Tetrahydro-8-isopropy-5-methyl-quinolin-3-yl)amino-2-imidazoline. The above amine (119 mg, 0.58 mmol) was mixed with 2-imidazolinesulfonic acid (180 mg, 1.20 mmol) in isobutyl alcohol (5 mL) aid heated at reflux for 2 days. The solvent was evaporated off to give a residue which was dissolved in CHCl$_3$ and flash chromatographed over silica gel (17 g) eluting with EtOAc/MeOH/Et$_3$N (20:3:1) to afford a white solid (129 mg, 81% yield). It was dissolved in EtOH and reated with fumaric acid (110 mg) in EtOH. Upon addition of ether and refrigeration, the solution gave white crystals (43 mg): mp 151°–154° C. Anal. Calcd. for C$_{16}$H$_{24}$N$_4$.1.6C$_4$H$_4$O$_4$: C, 58.73; H, 6.69; N, 12.23. Found: C, 58.41; H, 7.04; N, 12.24.

Example 16

2-(5,6,7,8-Tetrahydro-6,6-dimethyl-quinolin-3-yl)amino-2-imidazoline 5,6,7,8-Tetrahydro-6,6-dimethyl-3-nitro-quinoline. 4,4-Dimethyl-2-cyclohexen-1-one (500 mL, 3.80 mmcL) was mixed with 10% Pd-C (50 mg) and hydrogenated at 1 atm in MeOH (5 mL) for 2 h. Filtration through Celite gave a colorless oil (430 mg). It was mixed with 1-methyl-3,5-dinitio-2-pyridone (679 mg, 3.41 mmol) in 1M methanolic ammonia (68 mL, 68 mmol) and heated at reflux for 3 h. The solvent was evaporated off and the residue was suspended in CHCl$_3$ and flash chromatographed over silica gel (30 g) eluting with EtOAc/hexane (1:15) to afford a white solid (195 mg, 25% yield): rap 99°–101° C.

3-Amino-5,6,7,8-tetrahydro-6,6-dimethylquinoline. The above solid (195 mg, 0.95 mmol) was dissolved in MeOH (4.5 mL), treated with 10% Pd-C (20 mg) and hydrogenated at 1 atm for 2 h. Filtration through Celite gave a sticky greyish solid (162 mg, 97% yield).

2-(5,6,7,8-Tetrahydro-6,6-dimethyl-quinolin-3-yl)amino-2-imidazoline. The above amine (162 mg, 0.92 mmol) was mixed with 2-imidazolinesulfonic acid (276 mg, 1.84 mmol) in isobutyl alcohol (5 mL) and heated at reflux for 3 days. The solvent was evaporated off to give a residie which was dissolved in CHCl$_3$ and flash chromatographed over silica gel (19 g) eluting with EtOAc/MeOH/Et₃N (10:2:1) to afford a white foam (196 mg, 87% yield). It was dissolved in EtOH and treated with fumaric acid (186 mg) in EtOH. The solvent was removed and the residue was recrystallized from 2-propanol to afford a pale yellow solid (158 mg): mp 186°–188° C. (dec.). Anal. Calcd. for $C_{14}H_{20}N_4 \cdot 1.5C_4H_4O_4$: C, 57.41; H, 6.26; N, 13.39. Found: C, 57.24; H, 6.26; H, 13.15.

Example 17

2-(5,6,7,8-Tetrahydro-8,8-dimethyl-quinolin-3-yl) amino-2-imidazoline 5,6,7,8-Tetrohydro-8,8-dimethyl-3-nitro-quinolne. 2,2-Dimethyl-2-cyclohexanone (317 mg, 2.51 mmol) was mixed with 1-methyl-3,5-dinitro-2-pyridone (500 mg, 2.51 mmol) in 1M methanolic ammonia (50 mL, 50 mmol) and heated at reflux overnight. The solvent was evaporated off and the residue was suspended in CHCl₃ and flash chromatographec over silica gel (33 g) eluting with EtOAc/hexane (1:20) to afford a colorless oil (414 mg, 80% yield).

3-Amino-5,6,7,8-tetrahydro-6,6-dimthylethylquilno. The above oil (410 mg, 1.99 mmol) was dissolved in MeOH (6 mL), treated with 10% Pd-C (42 mg) and hydrogenated at 1 atm for 5 h. Filtration through Celite gave a sticky pinkish solid (320 mg, 91% yield).

2-(5,6,7,8-Tetrahydro-8,8-dimethyl-quinolin-3-yl) iamino-2-imidazoline. The above amine (175 mg, 0.99 mmol) was mixed with 2-imidazolinesulfonic acid (300 mg, 2.00 mmol) in isobutyl alcohol (6 mL) and heated at reflux for 2 days. The solvent was evaporated off to give a residue which was dissolved in CHCl₃ and flash chromatographed over silica gel (19 g) eluting with EtOAc/MeOH/Et₃N (20:3:1) to afford a sticky white solid (169 mg, 70% yield). It was dissolved in EtOH and treated with fumaric acid (160 mg) in EtOH. Upon the addition of ether and refrigeration, the solution gave white crystals (145 mg): mp 185°–186° C. (dec.). Anal. Calcd. for $C_{14}H_{20}N_4 \cdot 1.5C_4H_4O_4$: C, 57.41; H, 6.26; N, 13.39 Found: C, 57.24; H, 6.57; N, 13.10.

Example 18

(R)-2-(5,6,7,8-Tetrahydro-6,8-dimethyimethano-quinolin-3-yl)amino-2-imidazoline (R)-3-Amino-5,6,7,8-Tetrahydro-6,8-dimethylmethano-quinoline. (R)-(+)-Nopinone (347 mg, 2.51 mmol) was mixed with 1-methyl-3,5-dinitro-2-pyridone (500 mg, 2.51 mmol) in 1M methanolic ammonia (50 mL, 50 mmol) and heated at reflux overnight. The solvent was evaporated off and the residue was suspended in CHCl₃. The soluble fraction was flash chromatographed over silica gel (20 g) eluting with EtOAc/hexane (1:10) to afford a colorless oil 303 mg). A portion (298 mg, 1.37 mmol) was dissolved in MeOH (5 mL), treated with 10% Pd-C (30 mg) and hydrogenated at 1 atm for 2 h. Filtration through Celite gave a pale yellow oil (176 mg). It was partitioned between 2N HCl₃ and CH₂Cl₂. The aqueous layer was washed once more with CH₂Cl₂ before it was basined with Na₂CO₃ solution and extracted with CH₂Cl₂ (3×4 mL) to give a white solid (45 mg, 10% yield)

(R)-2-(5,6,7,8-Tetrahydro-6,8-dimethylmethano-7quinolin-3-yl)amino-2-imidazoline. The above amine (45 mg 0.24 mmol) was mixed with 2-imidazolinesulfonic acid (72 mg 0.48 mmol) in isobutyl alcohol (4 mL) and heated at reflux or 3 days. The solvent was evaporated off to give a residue which was dissolved in CHCl₃ and flash chromatographed over silica gel (18 g) eluting with EtOAc/MeOH/Et₃N (10:2:1) to afford an oil (28 mg, 66% yield). It was dissolved in EtOH and treated with fumaric acid (25 mg) in EtOH. Upon the addition of ether and refrigeration, the solution gave an off-white solid (22 mg): mp 183°–185° C. (dec.). Anal. Calcd. for $C_{15}H_{20}N_4 \cdot C_4H_4O_4 \cdot 1/4H_2O$: C, 60.55; H, 6.55; N, 14.36. Found: C, 60.39; H, 6.87; N, 14.64.

Example 19

2-(6-Ethyl-6,7,8-tetrahydro-1,6-naphthyrid-3-yl) amino-2-imidazoline

6-Ethyl-5,6,7,8-tetrahydro-3-nitro-1,6-naphthyridine. 1-Ethyl-4-piperidone (500 mg, 3.93 mmol) was mixed with 1-methyl-3,5-dinitro-2-pyridone (392 mg, 1.97 miol) in 1M methanolic ammonia (40 mL, 40 mmol) and heated at reflux for 3 h. The solvent was evaporated off and the residue was suspended in CHCl₃ and flash chromatographed over silica gel (32 g) eluting with EtOAc to afford an orange solid (379 mg, 93% yield).

3-Amino-6-ethyl-5,6,7,8-tetrahydro-1,6-anphthyridine. The above solid (185 mg, 0.89 mmol) was dissolved in conc. HCl (3 mL), cooled by an ice water bath and treated with tin(II) chloride dehydrate (600 mg, 2.66 mmol) in conc. HCl (3 mL). The mixture was stirred at room temperature for 1 h before it was slowly poured into cold Na₂CO₃ solution. Extraction with CHCl₃/2-propanol (3:1) twice gave a light brown oil (114 mg, 72% yield).

2-(6-Ethyl-5,6,7,8-tetrahydro-1,6-naphthyrid-3-yl) amino-2-imidazoline. The above amine (114 mg, 0.64 mmol) was mixed with 2-imidazolinesulfonic acid (193 mg, 1.29 mmol) in isobutyl alcohol (5 mL) and heated at reflux for 2 days. The solvent was evaporated off to give a residue which was dissolved in CHCl₃ and flash chromatographed ove silica gel (19 g) eluting with EtOAc/MeOH/Et₃N (10:2:1) to afford a pale brown foam (75 mg, 48% yield). It was dissolved in EtOH and treated with fumaric acid (107 mg) in EtOH. The solvent was removed and the residue was recrystllized from MeOH/ether to give an off-white solid (52 mg). Anal. Calcd. for $C_{13}H_{19}N_5 \cdot 5/2C_4H_4O_4 \cdot 1/3C_3H_8O \cdot 1/2H_2O$: C, 51.06; H, 5.83; N, 12.41. Found: C, 51.34; H, 5.77; N, 12.17.

Example 20

2-(5,6,7,8-Tetrahydroquinolin-3-yl)amino-2-imidazoline 5,6,7,8-tetrahydro-3-nitro-quinoline. A mixture of 1-methyly-3,5-dinitro-2-pyridone (2.4 g, 0.012 mole), cyclohexanone (1.18 g, 0.012 mole) and ammonia solution (2.0M, 120 mL) in methanol was refluxed overnight. The solvent was removed in vacuo and the residue was dissolved in ethyl acetate. The soluble portion was flash chromatographed over silica gel (eluent: 90:10 v/v ethyl acetate-hexane) to give a yellow solid (2.02 g, 94% yield).

3-Amino-5,6,7,8-tetrahydroquinoline. A solution of the above solid (0.541 g, 3.0 mmole) in methanol (40 ml) was subjected to hydrogenation with a H₂ balloon in the presence of 10% palladium on carbon. The reaction was carried out at room temperature overnight. The catalyst was then filtered off and the solvent was removed in vacuo to give a gray solid (0.44 g, 98% yield).

2-(5,6,7,8-Tetrahydroquinolin-3-yl)amino-2-imidazoline. A mixture of the above solid (0.221 g, 1.49 mmole), 2-imidazoline-2-sulfonic acid (0.805 g, 5.4 mmole) and isobutyl alcohol (4 mL) was refluxed for 18 hours. The solvent was removed in vacuo and the residue was flash chromatographed over silica gel (eluent: 10:2:1 v/v/v ethyl acetate-methanol-triethylamine). The product was obtained in 100% yield (0.337 g) as a pale yellow solid. The above solid was treated in ethanol with 1.0 equivalent of fumaric acid to give a fumarate as a white solid (59% yield): mp 201°–203° C. Anal. Calcd. for $C_{12}H_{16}N_4 \cdot 1.5C_4H_4O_4 \cdot 0.5H_2O$: C, 54.13; H, 5.76; N, 14.04. Found: C, 54.04; H, 5.96; N, 13.69.

Example 21

2-(2,3-Cyclopentenopyrid-5-yl)amino-2-imidazoline 2,3-Cyclopenteno-5-nitropyridine. A mixture of 1-methyl-3,5-dinitro-2-pyridone (1.2 g, 6.0 mmole), cyclopentanone (0.5 g, 6.0 mmole) and ammonia solution in methlnol (2.0M, 60 mL) was refluxed overnight. The solvent was removed in vacuo and the residue was dissolved in ethyl acetate. The soluble portion was flash chromatographed ovei silica gel (eluent: 90:10 v/v ethyl acetate-hexane). The product was obtained as a yellow solid (0.623 g, 63% yield 5-Amino-2,3-cyclopentenopyridine. A solution of the above solid (0.451 g, 2.75 mmole) in methanol (40 mL) was subjected to hydrogenation with a $H_2$ balloon in the presence of 10% Palladium on carbon. The reaction was carried out at room temperature for 4 h. The catalyst was then filtered off and the solvent was removed in vacuo to give a gray solid (0.36 g, 98% yield).

2-(2,3-Cyclopentenopyrid-5-yl)amino-2-imidazoline. A mixture of the above solid (0.18 g, 1.34 mmole), 2-imidazoline-2-sulfonic acid (0.70 g, 4.67 mmole) and isobutyl alcohol (3 mL) was refluxed overnight. The solvent was removed in vacuo and the residue was flash chromatographed over silica gel (eluent: 10:2:1 v/v/v ethyl acetate-methanol-triethylamine). The product was obtained in 92% yield (0.25 g) as a pale yellow solid. It was treated in ethanol with 1.2 equivalents of fumaric acid to give a fumarate salt as a white solid (59% yield): mp 182.0°–183.5° C. Anal. Calcd. for $C_{11}H_{14}N_4 \cdot 1.5C_4H_4O_4 \cdot 0.25H_2O$: C 53.61; H 5.39; N 14.72. Found: C 53.47; H 5.70; N 14.80.

Example 22

2-(5,8-Methano-5,6,7,8-tetrahydroquinolin-3-yl)amino-2-imidazoline 5,6,7,8-Tetrahydro-5,8-methano-3-nitroquinoline. A mixture of 1-methyl-3,5-dinitro-2-pyridone (0.3 g, 4.0 mmole), norcamphor (0.83 g, 7.5 mmole) and ammonia solution in methanol (2.0M, 40 mL) was refluxed for 3 hours. The solvent was removed in vacuo and the residue wa dissolved in ethyl acetate. The soluble portion was flash chromatographed over silica gel (eluent: 85:15 v/v ethyl acetate-hexane) to give a yellow solid It was recrystallized from ethyl acetate to afford yellow crystals (0.148 g, 21% yield)

3-Amino-5,6,7,8-Tetrahydro-5,8-methano-quinoline. A solution of the above crystals (0.148 g, 0.8 mmole) in methanol (40 mL) was subjected to hydrogenation with a $H_2$ balloon in the presence of 10% palladium on carbon. The reaction was carried out at room temperature overnight. The catalyst was then filtered off and the solvent was removed in vacuo. The product was obtained as a gray sold (0.059 g, 48% yield).

2-(5,8-Methano-5,6,7,8-tetrahydroquinolin-3-yl)amino-2-imidazoline. A mixture of the above solid (0.59 g, 0.40 mmole), 2-imidazoline-2-sulfonic acid (0.25 g, 0.167 mmole) and isobutyl alcohol (3 mL) was refluxed overnight.

The solvent was removed in vacuo and the residue was flash chromatographed over silica gel (eluent: 10:2:1 v/v/v ethyl acetate-methanol-triethylamine). The product was obtained in 80% yield (0.069 g) as a pale yellow solid. It was treated in isopropyl alcohol with 1.0 equivalent of fumaric acid to give a fumarate salt as a yellow solid (44% yield): mp 164.0°–166.0° C. Anal. Calcd. for $C_{12}H_{16}N_4 \cdot 1.5C_4H_4O_4 \cdot 0.25H_2O$: C, 56.09; H, 5.53; N, 13.78. Found: C, 56.01; H, 5.47; N, 13.78.

Example 23

2-(6-Benzyl-5,6,7,8-tetrahydro-1,6-naphthyrid-3-yl)amino-2-imidazoline

6-Benzyl-5,6,7,8-tetrahydro-3-nitro-1,6-naphthyridine. A mixture of 1-methyl-3,5-dinitro-2-pyridone (1.2 g, 6.0 mmol), 1-benzyl-4-piperidone (1.12 g, 5.9 mmol) and ammonia solution in methanol (2.0M, 60 mL) was refluxed for 3 h. The solvent was removed in vacuo and the residue was dissolved in ethyl acetate. The soluble portion was flash chromatographed over silica gel (eluent: 90:1 v/v ethyl acetate-hexane) to give a yellow solid (0.79 g, 49.7% yield).

3-Amino-6-benzyl-5,6,7,8-tetrahydro-1,6-naphthyridine. A solution of the above solid (0.79 g, 2.94 mmol) in methanol (100 mL) was subjected to hydrogenation with a $H_2$ balloon in the presence of 10% palladium on carbon. The reaction was carried cut at room temperature overnight. The catalyst was then filtered off and the solvent was removed in vacuo. The product was obtained as a gray solid (0.753 g, 100% yield).

2-(6-Benzyl-5,6,7,8-tetrahydro-1,6-naphthyrid-3-yl)amino-2-imidazoline. A mixture of the above solid (0.478 g, 2.0 mmol), 2-imidazoline-2-sulfonic acid 0.9 g, 6.0 mmol) and isobutyl alcohol (3 mL) was refluxed overnight. The solvent was removed in vacuo and the residue was flash chromatographed over silica gel (eluent: 10:2:1 v/v/v ethyl acetate-methanol-triethylamine). The product was obtained in 92% yield (0.565 g) as a pale yellow solid. It was treated in isopropyl alcohol/diethyl ether with 2.0 equivalents of fumaric acid to give a fumarate salt as a yelloo solid (44% yield). Anal. Calcd. for $C_{18}H_{21}N_5 \cdot 1.5C_4H_4O_4 \cdot 1.5H_2O$: C, 56.69; H, 5.91; N, 13.78. Found: C, 56.65; H, 5.77; N, 14.01.

Example 24

2-(5,6,7,8-tetrahydro-6-oxa-quinolin-3-yl)amino-2-imidazoline 5,6,7,8-tetrahydro-3-nitro-6-oxa-quinoline. A mixture of 1-methyl-3,5-dinitro-2-pyridone (0.8 g, 4 mmol), tetrahydro-4H-pyran-4-one (0.4 g, 4 mmol) and ammonia solution in methanol (2.0M, 40 mL) was refluxed for 4 h. The solvent was removed in vacuo and the residue was dissolved in ethyl acetate. The soluble portion was flash chromatocraphed over silica gel (eluent: 90:10 v/v ethyl acetate-hexane) to give a yellow solid (O.376 g, 52% yield).

3-Amino-5,6,7,8-tetrahydro-6-oxa-quinoline. A mixture of the above solid (0.37 g, 2.05 mmol), tin chloride dihydrate (1.17 g, 5.2 mmol) and hydrochloric acid (37% aqueous solution, 15 mL) was stirred at room temperature overnight and then neutralized with sodium hydroxide solution to pH=8. The product was extracted with ethyl acetate. The organic phase was evaporated in vacuo to give a white solid (0.232 g, 75% yield).

2-(5,6,7,8-tetrahydro-6-oxa-quinolin-3-yl)amino-2-imidazoline. A mixture of the above solid (0.232 g, 0.55 mmol), 2-imidazoline-2-sulfonic acid (0.7 g, 4. 7 mmol) and isobutyl alcohol (3 mL, was refluxed for 3 days. The solvent was removed an vacuo and the residue was flash chromatographed over silica gel (eluent: 10:2:1 v/v/v ethyl acetate-methanol-triethylamine). The product was obtained in 92.6% yield (0.312 g). It was treated in ethaiol with 1.0 equivalent of fumaric acid to give a fumarate as a white crystal (47% yield): mp 201°–202.5° C. Anal. Calcd. for $C_{11}H_{14}N_4 \cdot 1.5C_4H_4O_4$: C, 52.04; H, 5.10; N, 14.29 Found: C, 51.86; H, 5.12; N, 14.03.

Example 25

2-(5,6,7,8-tetrahydro-6-thia-quinolin-3-yl)amino-2-imidazoline 5,6,7,8-tetrahydro-3-nitro-6-thia-quinoline. A mixture of 1-methyl-3,5-dinitro-2-pyridone (0.6 g, 3.0 mmol), tetrahydrothiopyran-4-one (0.35 g, 3.0 mmol) and ammonia solution in methanol (2.0M, 30 mL) was refluxed for 6 h. The solvent was removed in vacuo and the residue was dissolved in ethyl acetate. The soluble portico was flash chromatographed over silica pel (eluent: 90:1 v/v ethyl acetate-hexane) to give a yellow solid (0.586 g, 99% yield).

3-Amino-5,6,7,8-tetrahydro-6-thia-quinoline. A mixture of the above solid (0.29 g, 1.48 mmol), tin chloride dihydrate (0.83 g, 3.68 mmol) and hydrochloric acid (37% aqueous solution, 15 mL) was stirred at room temperature overnight and then neutralized with sodium hydroxide solution to pH=8. The product was extracted with ethyl acetate. The organic phase was concentrated in vacuo to give a white solid (0.20 g, 81.6% yield).

2-(5,6,7,8-tetrahydro-6-1thia-quinolin-3-yl)amino-2-inidazoline. A mixture of the above solid (0.200 g, 1.20 mmol), 2-imidazoline-2-sulfonic acid (0.54 g, 3 6 mmol) and isobutyl alcohol (3 mL) was refluxed for one day. The solvent was removed in vacuo and the residue was column cnromatographed over silica gel (eluent: 10:2:1 v/v/v ethyl acetate-methanol-triethylamine). The product was obtained in 100% yield (0.313 g). It was treated in ethaiol with 1.0 equivalent of fumaric acid to give a fumarate salt as white crystals (50% yield): mp 199.5°–200.5° C. Anal Calcd. for $C_{11}H_{14}N_4S \cdot 1.5C_4H_4O_4$: C, 50.00; H, 4.90; N, 13.73. Found: C, 49.85; H, 4.78; N, 13.58.

Example 26

2-(5,6-Dihydro-7,7-Dimethyl-cyclopenta[b]pyrid-3-yl)amino-2-imidazoline 5,6-Dihydro-7,7-Dimethyl-3-nitro-cyclopenta[b]pyridine. A mixture of 1-methyl-3,5-dinitro-2-pyridone (0.8 g, 4.0 mmol), 2,2-dimethyl-cyclopentanone (0.45 g, 4.0 mmol) and ammonia solution (2.0M) in methanol (40 mL) was refluxed overnight. The solvent was removed in vacuo and the residue was dissolved in ethyl acetate. The soluble portion was flash chromatographed over silica gel (eluent 90:10 v/v ethyl acetate-hexane) to give a yellow solid (0.183 g, 24% yield).

3-Amino-5,6-dihydro-7,7-Dimethyl-cyclopenta[b]pyridine. A solution of the above solid (0.183 g, 0.9 mmol) in methanol (40 mL) was subjected to hydrogenation with a $H_2$ balloon in the presence of 10% palladium on carbon. The reaction was carried out at room temperature overnight. The catalyst was then filtered off and the solvent was removed in vacuo. The product was obtained in 100% yield.

2-(5,6-Dihydro-7,7-Dimethyl-cyclopenta[b]pyrid-3yl) amino-2-imidazoline. A mixture of the above intermediate (0.154 g, 0.95 mmol), 2-imidazoline-2-sulfonic acid (0.40 g, 2.67 mmol) and isobutyl alcohol (3 mL) was refluxed overnight. The solvent was removed in vacuo and the residue was flash chromatographed over silica gel (eluent: 10:2:1 v/v/v ethyl acetate-methanol-triethylamine). The product was obtained in 47% yield (0.103 g). It was treated in ethanol with 2 equivalents of fumaric acid to give a fumarate salt as a yellow solid (34% yield): mp 191.5°–193° C. Anal. Calcd. for $C_{13}H_{18}N_4 \cdot 1.5C_4H_4O_4 \cdot 0.2H_2O$: C, 55.93; H, 6.03; N, 13.73. Found: C, 56.26; H, 6.41; N, 13.39.

Example 27

2-(2,3-Cyclopenteno-1-oxido-5-pyri(yl)amino-2-imidazoline

A mixture of 2-(2,3-Cyclopentenopyrid-5-yl)amino-2-imidazoline (0.1 g, 0.5 mmol), hydrogen peroxide (30% aqueous solution, 0.1 mL) and acetic acid (5 mL) was heated at 90°–100° C. for 10 h. Another 0.1 mL of hydrogen peroxide was added. The reaction was complete after heating at 90°–100° C. overnight. The solvent was removed in vai uo and the residue was flash chromatographed over silica gel (eluent: 10:2:1 v/v/v ethyl acetate-methanol-triethylamine). The product was obtained in 95% yield (0.102 g). It was treated in ethanol with one equivalent of fumaric acic to give a fumarate salt as a white solid (54% yield). Anal. Calcd. for $C_{11}H_{14}N_4O \cdot 1.2C_4H_4O_4$: C, 53.08; H, 5.30; N, 15.67. Found: C, 52.87; H, 5.16; N, 15.89.

Example 28

2-(2-Bromo-5,6-cyclopenteno-3-pyridyl)amino-2-imidazoline

A mixture of 2-(2,3-Cyclopentenopyrid-5-yl)amino-2-imidazoline (0.12 g, 0.59 mmol), bromine (0.4 mL) and acetic acid (3 mL) was stirred at room temperature overnight. The acetic acid was then removed in vacuo and the residue was basified with an ammonia solution (2.0M) in methanol to pH=8. The solvent was evaporated. The product was separated by flash chromatography (eluent: 10:2:1 v/v/v ethyl acetate-methanol-triethylamine) to give the prcduct in 36% yield (0.060 g). It was treated in ethanol with 2 equivalents of fumaric acid to give a fumarate salt as a white solid (79% yield): mp 234°–235° C. Anal. Calcd. for $C_{11}H_{13}BrN_4 \cdot 0.65C_4H_4O_4 \cdot 0.33C_2H_6O$: C, 46.06; H, 4.76 N, 15.08. Found: C, 45.85; H, 4.71; N, 15.07.

Example 29

2-(2,4-Dibromo-5,6-cyclopentenopyrid-3-yl)amino-2-imidazoline

3-Amino-2,4-Dibromo-5,6-cyclopentenopyridine. A mixture of 5-amino-2,3-cyclopentenopyridine (0.12 g, 0.9 mmol), bromine (0.2 mL) and acetic acid (10 mL) was stirred at room temperature for 2 h. The acetic acid was removei in vacuo. The product was separated by flash chromatograrhy (eluent: 80:20 v/v hexane-ethyl acetate) to give a white solid (0.12 g, 46% yield).

1-Acetyl-2-(2,4-Dibromo-5,6-cyclopentenopyrid-3 yl)amino-2-imidazoline. A mixture of the above solid (0.183 g, 0.63 mmol), N-acetyl-2-imidazolidone (0.1 g, 0.78 mmol) and phosphorus oxychloride (5 mL) was heated at about 55° C. overnight. The reaction solution was neutralized with saturated aqueous solution of sodium bicarbonate and then extracted with ethyl acetate. The organic phase was concentrated under reduced pressure. The solid residue was recrystallized from methanol/ethyl acetate to give a white solid (0.135 g, 54% yield).

2-(2,4-Dibromo-5,6-cyclopentenopyrid-3-yl)amino-2-imidazoline. A mixture of the above solid (0.135 g, 0.34 mmol) and saturated hydrogen chloride solution in ethanol (5 mL) was first stirred at room temperature overnight and then heated at 50° C. for 6 h. The solvent was evaporated and the residue was recrystallized from ethanol to give a hydrochloride salt as a light brown solid (0.28 g): mp 191°–194° C. Anal. Calcd. for $C_{11}H_{12}Br_2N_4$NHCl: C, 33.29; H, 3.27; N, 14.12. Found: C, 33.04; H, 3.66; N, 13.75. The supernatant was basified with 2.0M ammonia solution in methanol and evaporated to dryness. The residue was purified by flash chromatography (eluent: 10:2:1 v/v/v ethyl acetate-methanol-triethylamine) to give another 0.106 g of product as the free base. Total yield: 100%.

Example 30

2-(5,6-Cyclopenteno-2,4-dimethyl-pyrid-3-yl)amino-2-imidazoline

3-Amino-5,6-cyclopenteno-2,4-dimethylpyridine. To a dry pressure tube was added 3-Amino-2,4-Dibromo-5,6-cyclopentenopyridine (0.4 g, 1.37 mmol), tetramethyltin (0.56 mL, 4.0 mmol), anhydrous DMF (6 mL) and a catalytic amount of bis (triphenylphosphine)palladium(II) chloride. The tube was sealed under Argon protection, wrapped with aluminum foil and heated at 120°–140° C. overnight. The solvent was then removed in vacuo and the residie was flash chromatographed over silica gel (eluent: 10:2:1 v/v/v ethyl acetate-methanol-triethylamine) to give the product (0.219 g, 99% yield).

2-(5,6-Cyclopenteno-2,4-dimethyl-pyrid-3-yl) 1)amino-2-imidazoline. To a mixture of the above intermeciate (0.2 g, 1.23 mmol), sodium bicarbonate (1 g), chloroform (8 mL) and water (6 mL) was added th4ophosgene (1 mL). The solution was vigorously stirred at room temperature overnight and basified to pH 8 with saturated sodium bicarbonate solution. The organic layer was separated and concentrated to give a residue (0.261 g, 100% yield). A portion (0.25 g, 1.23 mmol) was mixed with ethylenediamine (1 mL) and methanol (10 mL), and was stirred at room temperature for 2 h. The solvent was then removed in vacuo and the residue was subjected to flash chromatography over silica gel (eluent: 100:20 v/v ethyl acetate-2.0M ammonia solution in methanol). The desired intermediate was thus obtained in 97% yield (0.309 g). This intermediate (0.309 g, 1.17 mmol) was dissolved in acetonitrile (5 mL) and stirred a 0° C. in the presence of 2-chloro-3-ethylbenzoxazolium tetrafluoroborate (0.38 g) for 4 h. Triethylamine (0.2 mL) was then added. The mixture was stirred for another 3 h. The solvent was removed in vacuo and the residue was purified by flash chromatography (eluent: 10:2:1 v/v/v ethyl acetate-methanol-triethylamine) to give the product in 46% yield (0.123 g). It was treated in ethanol with 2 equivalents of fumaric acid to give a fumarate salt as a white solid (53% yield): mp 220°–221° C. Anal. Calcd. for $C_{13}H_{18}N_4 \cdot 1.5 C_4H_4O_4$: C, 56.43; H, 5.98; N, 13.85. Found: C, 56.41; H, 6.13; N, 13.85.

Example 31

2-(5,6-Cyclopenteno-2,4-diethyl-3-pyridyl)amino-2-imidazoline

3-Amino-5,6-cyclopenteno-2,4-diethylpyridine. To a dry pressure tube was added 3-Amino-2,4-Dibromo-5,6-cyclopentenopyridine (0.4 g, 1.37 mmol), tetraethyltin (0.8 mL, 4.0 mmol), anhydrous DMF (6 mL) and a catalytic amount of bis(triphenylphosphine)palladium(II) chloride. The tube was sealed under Argon protection, wrapped with aluminum foil and heated at 120°–140° C. overnight. The solvent was then removed in vacuo and the residue was flash chromatographed over silica gel (eluent: 10:2:1 v/v/v ethyl acetate-methanol-triethylamine) to give the proiuct in 82% yield (0.212 g).

2-(5,6-Cyclopenteno-2,4-diethyl-3-pyridyl)amino-2-imidazoline. To a mixture of the above intermediate (0.126 g, 0.66 mmol), sodium bicarbonate (0.5 g), chloroform (5 mL) and water (5 mL) was added thiophosgene (0.3 mL). The solution was vigorously stirred at room temperature overnight and basified to pH 8 with saturated sodium bicarbonate solution. The organic layer was separated and concentrated to give a residue (0.180 g, 100% yield). A portion (0.154 g, 0.66 mmol) was mixed with ethylenediamine (0.44 mL) and methanol (10 mL), and was stirred at room temperature for 2 h. The solvent was then removed in vacuo and the residue was subjected to flash chromatography over silica gel (eluent: 10:2:1 v/v/v ethyl acetate-methanol-triethylamine) to give the desired intermediate in 92% yield (0.178 g). A solution of the intermediate (0 178 g, 0.61 mmol) in acetonitrile (5 mL) was stirred at 0° C. in the presence of 2-chloro-3-ethylbenzoxazolium tetrafluoroborate (0.19 g) for 4 h. Triethylamine (0.2 mL) was then added. The mixture was stirred for another 3 h. The solvent was removed in vacuo and the residue was purified by flash chromatography (eluent: 10:2:1 v/v/v ethyl acetate-methanol-triethylamine) to give the product in 44% yield (0.070 g).

Example 32

4-(4,5-Dihydro-1H-imidazol-4-ylmethyl)-quinoline fumarate

Step A. 2-(Benzhydrylideneamino)-3-quinolin-4-yl-propionitrile. To N-(Diphenylmethylene)aminoacetonitrile (0.360 g, 1.633 mmol) in 10 ml of anhydrous THF and HMPA (hexamethyl phosphoramidite) (0.38 ml, 2.12 mmol), at −78° C., LDA (2.0M, 1.06 ml, 2.12 mmol) was added dropwise over a period of 5 minutes. The color of solution turns from colorless to yellow to dark brown. It was then stirred at −78° C. for one hour. 4-Chloromethylquinoline (0.29 g, 1.63 mmol) was added dropwise over a period of 5 minutes and the reaction mixture was slowly brought to room temperature over a period of five minutes. The reaction mixture was quenched by addition of ice and partitioned between EtOAc (20 ml) and water (5 ml). The organic layer was dried over sodium sulfate, filtered concentrated and column purified (hexanes:EtOAc; 3.5:1.5) to give 0.155 g (26%) of the product as a syrup, which was used as such for the subsequent step.

Step B. 2-Amino-3-quinolin-4-yl-propionitrile. To 2-(Benzhydrylideneamino)-3-quinolin-4-yl-propionitrile (0.155 g, 4.29 mmol) in 5 ml dioxane, 1N HCl (1.3 ml, 12.8 mmol) was added and the reaction mixture stirred at room temperature overnight. The solution was concentrated under reduced pressure, partitioned between 10 ml water and EtOAc (10 ml). The organic layer was dried over sodium sulfate filtered and concentrated to give 2-Amino-3-quinolin-4-yl-propionitrile 0.036 g (43%) which was used as such for the subsequent step.

Step C. 3-Quinolin-4-yl-propane-1,2-diamine. To 2-Amino-3-quinolin-4-yl-propionitrile (0.036 g, .0.18 mmol) in 10 ml of ethanol, ammonia gas was bubbled for 15 minutes. 1 g of Raney Ni (washed with 2×50 ml water and 2×50 ml ethanol) was added to the solution and the reaction r ixture was hydrogenated at 50 psi for 2 hours. The reaction mixture was filtered over celite and concentrated to give 0.250 g (50%) of the product which was used as such for the subsequent step.

Step D. 4-(4,5-Dihydro-1H-imidazol-4-ylmethyl)-quinoline. To 3-Quinolin-4-yl-propane-1,2-diamine (0.080 g, 3.98 mmol) in 5 ml of dry dichloromethane, formimidic acid ethyl ester hydrochloride (0.174 g, 7.96 mmol) (Ohme, R. et al. *Angew.Chem.Int.Engl.Ed.* 1967, 6, 90.) was added. The reaction mixture was stirred overnight at room temperature. Aqueous ammonia (2 ml) was added to the reaction mixture and was partitioned between EtOAc (2×5 ml) and water. The organic layer was dried, filtered and concentrated to give 0.084 g (100%) of the product as a syrup.

Step E. 4-(4,5-Dihydro-1H-imidazol-4-ylmethyl)-quinoline fumarate. To 4-(4,5-Dihydro-1H-imidazol-4-ylmethyl)-quinoline (0.76 g, 0.359 mmol) in 5 ml ethanol, fumaric acid (0.041 g, 0.359 mmol) was added and the solution was heated till all the fumaric acid dissolves. The reaction mixture was concentrated to yield 0.077 (100%) of a solid which was recrystallized from isopropanol: m.p. 180°–182° C.; Anal. Calcd. for $C_{13}H_{13}N_3 \cdot 1.5$ fumaric acid. 0.1 $H_2O$: C, 58.94; H, 5.00; N, 10.85. Found: C, 58.99; H. 5.03; N, 10.84.

Example 33

4-[1-(1H-Imidazol-4-yl)-ethyl]-quinoline dihydrochloride

Step A. 1-Quinolin-4-yl-ethanol. To 4-quinolinecarbaldehyde (2 g, 12.73 mmol) in 20 ml anhydrous ether, MeLi (1.4M, 10 ml, 13.9 mmol) was added dropwise over a period of five minutes at 0° C. The reaction iixture was stirred at room temperature for 3 hours. The solution was partitioned between ether (20 ml) and water (10 ml). The organic layer was dried over sodium sulfate, filtered and concentrated to give 1.43 g (59%) of the product which was then used as such for the subsequent step.

Step B. 4-(1-Chloroethyl)-quinoline. To 1-Quinolin-4-yl-ethanol (1.4 g, 8.09 mmol) in 15 ml chloroform, thionyl chloride (1.8 ml, 20.2 mmol) was added dropwise over a five minute period at room temperature. Stirring was continued for 30 minutes after which the reaction mixture aas cooled to 0° C. and quenched carefully by the addition of saturated aqueous $NaHCO_3$ (20 ml). The chloroform layer was dried over sodium sulfate, filtered and concentrated. Column purification (hexane:ethyl acetate; 1.5:3.5) gave 1.54 g (100%) of the product as a syrup which was used as such for the subsequent step.

Step C. 2-(Benzhydrylideneamino)-3-quinolin-4-yl-butyronitrile. To N-(Diphenylmethylene)aminoacetonitrile (2.26 g, 10.2 mmol) in 10 ml of anhydrous THF and HMPA (2.17 ml, 12.14 mmol), at −78° C., LDA (2.0M, 6.0 ml, 12.14 mmol) was added dropwise over a period of 5 minutes. The color of solution turns from colorless to yellow to dark brown. It was then stirred at −78° C. for one hour. Then 4-(1-Chloroethyl)-quinoline (1.79 g, 9.34 mmol) was added dropwise and the reaction mixture was slowly brought to room temperature over a period of five minutes, quenched by addition of ice and partitioned between EtOAc (20 ml) and water (5 ml). The organic layer was dried over sodium sulfate, filtered, concentrated and column purified (hexanes:EtOAc; 3.5:1.5) to give 3.0 g (86%) of the product as a syrup which was used as such for the subsequent step.

Step D. 2-Amino-3-quinolin-4-yl-butyronitrile. To 2-(Benzhydrylideneamino)-3-quinolin-4-yl-butyronitrile (3.0 g, 7.3 mmol) in 30 ml dioxane, 1N HCl (30 ml, 29.99 mmol) was added and the reaction mixture stirred at room temperature overnight. The solution was then concentrated under reduced pressure, partitioned between water (10 ml) and EtOAc (10 ml). The organic layer was dried over sodium sulfate, filtered and concentrated to give 1.58 g (88%) of the product which was used as such for the subsequent step.

Step E. 3-Quinolin-4-yl-butane-1,2-diamine. To 2-Amino-3-quinolin-4-yl-butyronitrile (1.58 g, 6.42 mmol) in 10 ml of ethanol, ammonia gas was bubbled for 15 minutes. 2 g of Raney Ni (washed with 2×50 ml water and 2×50 ml ethanol) was added to the solution and the reaction mixture was hydrogenated at 50 psi for 2 hours, filtered over celite and concentrated to give 1.54 a (96%) of the product which was then used as such for the subsequent step.

Step F. 4-[1-(4,5-Dihydro-1H-imidazol-4-yl)-ethyl]quinoline. To 3-Quinoilin-4-yl-butane-1,2-diamine (1.54 g, 7.16 mmol) in 5 ml of dry dichloromethane, formimidic acid ethyl ester hydrochloride (1 57 g, 14.3 mmol) was added. The reaction mixture was stirred overnight at room temperature. Aqueous ammonia (2 ml) was added to the reaction mixture and was partitioned between EtOAc (2×5 ml) and water. The organic layer was dried, filtered and concentrated to give 1.16 g (73%) of the product as a syrup which was used for the subsequent step.

Step G. 4-[1-(1H-Imidazol-4-yl)-ethyl]-quinoline. To oxalyl chloride (0.85 µl, 0.976 mmol) in 5 ml of anhydrous dichloromethane at −78° C., dimethylsulfoxide (0.14 ml, 1.95 mmol) was added over a five minute period. After stirring for 5 minutes at the same temperature, 4-[1-(4,5-Dihydro-1H-imidazol-4-yl)-ethyl]quinoline (0.200 g, 0.888 mmol) was added slowly and the reaction mixture was stirred for a further 20 minutes at −78° C. Triethylamine (0.62 ml, 4.44 mmol) was added and the reaction mixture was stirred for 5 minutes at −78° C. and then 20 minutes at room temperature. The reaction mixture was concentrated under reduced pressure and partitioned between EtOAc (10 ml) and water (5 ml). The organic layer was dried over sodium sulfate filtered, concentrated and column purified [EtOAc:MeOH:Methanol $NH_3$ (1.0M); 3.5:1:0.5) to give 0.100 g (51%) of the product as a syrup.

Step H. 4-[1-1H-Imidazol-4-yl)-ethyl]-quinoline dihydrochloride. To 4-[1-(1H-Imidazol-4-yl)-ethyl]-quinoline (0.067, 0.300 mmol) in 5 ml methanol, 3 ml of HCl in dioxane was added and the reaction mixture was concentrated under reduced pressure to give 0.0.067 g, (100%) of the product as a pale yellow solid which was recrystallized from isopropanol: m.p. 276°–278° C.; Anal. Calcd. for $C_{14}H_{15}N_3Cl_2$ 0.6 mole $H_2O$: C, 54.77; H, 5.32; N, 13.69. Found: C, 54.93; H, 4.94; N, 13.28.

Example 34

4-[1-(1H-Imidazol-4-yl) -propyl]-quinoline dihydrochloride

Step A. 4-[1-(1H-Imidazol-4-yl)-propyl]-quinoline. This compound was prepared starting from 4-quinolinecarboxaldehyde using experimental conditions outlined for example 33, except for substituing MeLi in step A with EtMgBr.

Step B. 4-[1-(1H-Imidazol-4-yl)-propyl]-quinoline dihydrochloride. To 4-[1-(1H-Imidazol-4-yl)-propyl]-quinoline (0.185, 0.779 mmol) in 5 ml methanol, 3 ml of HCl in dioxane was added and the reaction mixture was concentrated under reduced pressure to give 0.240 g, (100%) of the product as a foam.

Example 35

4-[1-(1H-Imidazol-4-yl)-ethyl]-2-methyl-quinoline dihydrochloride

Step A. 4-[1-(1H-Imidazol-4-yl)-ethyl]-2-methyl-quinoline. This compound was prepared starting from 2-Methyl-4-quinolinecarbaldehyde (Minisci, F. et al. *J. Org. Chem.* 1986, 51, 536) and using experimental conditions outlined for example 33.

Step B. 4-[1-(1H-Imidazol-4-yl)-ethyl]-2-methyl-quinoline dihydrochloride. To 4-[1-(1H-Imidazol-4-yl)- ethyl]-2-methyl-quinoline (0.062, 0.261 mmol) in 5 ml methanol, 3 ml of HCl in dioxane was added and the reaction mixture was concentrated under reduced pressure to give 0.080 g,(100%) of the product as a pale yellow solid which was crystallized from isopropaanol-ether: m.p. 238°–240° C.; Anal Calcd. for $C_{15}H_{17}N_3Cl_2$ 1.0 mole $H_2O$: C, 54.86; H, 5.82. Found: C, 54.83; H, 5.99.

Example 36

4-[1-(1H-Imidazol-4-yl)-ethyl]-2-phenylquinoline dihydrochloride

Step A. 1-(2-phenylquinolin-4-yl)-ethanone. To methyl 2-phenyl-4-quinolinecarhoxylate (1 g, 3.80 mmol) in 10 ml ether, at 0° C. was added MeLi (1.4M, 3.0 ml, 4.1 mmol) dropwise over a five minute period. The reaction mixture was stirred at 0° C. for 30 minutes and quenched by the addition of 10 ml of water. The ether layer was separated, dried over sodium sulfate, filtered, concentrated and column purified (hexane:EtOAc; 4.5:0.5) to give 0.233 g (23%) of the product as a syrup which was used as such for the subsequent step.

Step B. 1-(2-phenylquinolin-4-yl)-ethanol. To 1-(2-phenylquinolin-4-yl)-ethanone (0.233 g, 0.943 mmol) in 5 ml methanol, at room temperature sodium borohydride (0.036 g, 0.943 mmol) was added and the solution stirred for 30 minutes. The reaction mixture was concentrated and partitioned between EtOAc (10 ml) and water (5 ml). The organic layer was dried over sodium sulfate, filtered, concentrated and column purified (hexane:EtOAc; 3.5:1.5) to give 0.145 g (62%) of the product as a syrup which was used as such for the subsequent step.

Step C. 4-[1-(1H-Imidazol-4-yl)-ethyl]-2-phenyl-quinoline. This compound was prepared starting from 1-(2-phenylquinolin-4-yl)-ethanol (step B) and following experimental conditions outlined for example 33.

Step D. 4-[1-(1H-Imidazol-4-yl)-ethyl]-2-phenyl-quinoline dihydrochloride. To 4-[1-(1H-Imidazol-4-yl)-ethyl]-2-phenyl-quinoline (0.02 g, 0.066 mmol) in 5 ml methanol, 3 ml of HCl in dioxane was added and the reaction mixture was concentrated under reduced pressure to give 0.025 g, (100%) of the product as a pale yellow solid which was crystallized from isopropanol-ethyl acetate: m.p. 175°–180° C.; Anal. Calcd. for $C_{20}H_{19}N_3Cl_2$ 1.0 mole $H_2O$: C, 64.52; H,5.14; N, 11.29. Found: C, 64.83; H, 5.59; N, 11.23.

Example 37

4-[1-(1H-Imidazol-4-yl)-ethyl]-isoquinoline dihydrochloride

Step A. 4-[1-(1H-Imidazol-4-yl)-ethyl]-isoquinoline. This compound was prepared starting from Isoquinoline-4-carbaldehyde (Minisci, F. et al. *J. Org. Chem.* 1986, 51, 536) and using experimental conditions outlined for example 33.

Step B. 4-[1-(1H-Imidazol-4-yl)-ethyl]-isoquinoline dihydrochloride. To 4-[1-(1H-Imidazol-4-yl)-ethyl]-isoquinoline (0.105, 0.470 mmol) in 5 ml methanol, 3 ml of HCl in dioxane was added and the reaction mixture was concentrated under reduced pressure to give 0.105 g, (86%) of the product as a brown solid which was crystallized from isopropanol: m.p. 185°–190° C.; Anal. Calcd. for $C_{14}H_{15}N_3Cl_2$ 0.9 mole $H_2O$: C, 53.82; H, 5.42; N, 13.45. Found: C, 54.01; H, 5.77. N. 13.98.

Example 38

4-[1-(1H-Imidazol-4-yl)-propyl]-isoquinoline dihydrochloride

Step A. 4-[1-(1H-Imidazol-4-yl)-propyl]-isoquinoline. This compound was prepared starting from Isoquinoline-4-carbaldehyde and using experimental conditions outlined for example 33 except for substituting MeLi in step A with EtMgBr.

Step B. 4-[1-(1H-Imidazol-4-yl)-propyl]-isoquinoline dihydrochloride. To 4-[1-(1H-Imidazol-4-1)-propyl]-isoquinoline (0.077 g, 0.324 mmol) in 5 ml methanol, 3 ml of HCl in dioxane was added and the reaction mixture was concentrated under reduced pressure to give 0.086 g, (86%) of the product as a yellow solid which was crystallized from isopropanol-ether: m.p. 173°–176° C.; Anal. Calcd. for $C_{15}H_{17}N_3Cl_2$ 0.6 mole dioxane: C, 55.39; Hz, 5.70, N, 11.54. Found: C, 55.85; H, 6.09; N, 11.15.

Example 39

(1H-Imidazol-4-yl)-quinolin-4 yl-methanol dihydrochloride

Step A. 2-(tert-Butyldimethylsilyl)-4-(hydroxyquinolin-4-yl-methyl)-methyl)-imidazole-1-sulfonic acid dimethylamide. To N,N-dimethylsulfamoyl-2-(tert-butyldimethylsilyl)imidazole (0.165 g, 1.05 mmol) (Chadwick, D. J. et al. *J.Chem.Soc.Perkin Trans. I*. 1984, 481) in 8 ml THF, n-BuLi (0.55 ml, 1.1 mmol) was added over a period of 5 minutes at –78° C. and the reaction mixture was stirred for 30 minutes at the same temperature. 4-quinolinecarbaldehyce (0.165 g, 1.05 mmol) was added neat to the solution and the reaction mixture was stirred for 10 minutes at –78° C. and then at room temperature for 30 minutes. The reaction mixture was partitioned between EtOAc (50 ml) and water (10 ml). The organic layer was dried over sodium sulfate, filtered and concentrated to yield 0.462 g (100%) of the product.

Step B. (1H-Imidazol-4-yl)-quinolin-4-yl-methanol. To (1H-Imidazol-4-yl)-quinolin-4-yl-methanol (0.150 g, 0.32 mmol) 7 ml of 1.5N HCl was added and the contents refluxed for 2 hours. The reaction mixture was concentrated, partitioned between water(10 ml) and EtOAc (2×10 ml). The organic layer was dried over sodium sulfate, filtered , concentrated and column purified ($CH_2Cl_2$: MeOH: Methanol-$NH_3$ (1.0M) (4.5:0.25:0.25) to yield 0.072 g (100%) of the product.

Step C. (1H-Imidazol-4-yl)-quinolin-4-yl-methanol dihydrochlcride. To (1H-Imidazol-4-yl)-quinolin-4-yl-methanol (0.030 g, 0.133 mmol) in 5 ml methanol, 3 ml of HCl in dioxane was added and the reaction mixture was concentrated under reduced pressure to give 0.33 g, (85%) of the product as a solid: m.p. 200°–202° C.; Anal. Calcd. for $C_{13}H_{13}N_3OCl_2$ 1.0 $H_2O$: C, 49.38; Hz, 4.78; N, 13.29. Found: C, 49.52; H 4.72; N 13.52.

Example 40

4-[(1H-Imidazol-4-yl)-methoxymethyl]quinoline dihydrochloride

Step A. 2-(tert-Butyldimethylsilyl)-4-(methoxyquinolin-4-yl-methyl)-imidazole-1-sulfonic acid dimethylamide. To pentane washed sodium hydride (0.048 g, 1.2 mmol) in 5 ml of THF at 0° C., 2-(tert-Butyldimethylsilyl)-4-(hydroxyquinolin-4-yl-methyl)-imidazole-1-sulfonic acid dimethylamide (example 8, step A) (0.375 g, 0.811 mmol) was added slowly over a period of 5 minutes. After stirring at room temperature for 15 minutes, it was again cooled to 0° C. and methyl iodide (0.1 ml, 1.62 mmol) was added neat. The reaction mixture was stirred at room temperature for 1 hour, concentrated under reduced pressure and partitioned between EtOAc (10 ml) and water (10 ml). The organic layer was dried over sodium sulfate, filtered and concentrated to yield 0.32 g (83%) of the product as a syrup.

Step B. 4-[(1H-Imidazol-4-yl)-methoxymethyl]quinoline. To 2-(tert-Butyldimethylsilyl)-4-(methoxyquinolin-4yl-methyl)-imidazole-1-sulfonic acid dimethylamide. (0.32 g, 0.672 mmol), 7 ml of 1.5N HCl was added and the solution refluxed for two hours. The reaction mixture was concentrated, partitioned between water(10 ml) and EtOAc (2×10 ml). The organic layer was dried over sodium sulfate, filtered concentrated and column purified ($CH_2Cl_2$: MeOH: methanol-$NH_3$ (1.0M); (4.5:0.25:0.25) to yield 0.160 g (100%) of the product as a syrup.

Step C. 4-[(1H-Imidazol-4-yl)-methoxymethil]quinoline dihydrochloride. To 4-[(1H-Imidazol-4-yl)-methoxymethyl] quinoline (0.160 g, 0.66 mmol) in 5 ml methanol, 3 ml of HCl in dioxane was added and the reaction mixture was concentrated under reduced pressure to give 0.116 g, (80%) of the product as a white solid: m.p. 188°–190° C.; Anal. Calcd. for $C_{14}H_{15}N_3OCl_2$ 0.6 mole $H_2O$: C, 52.06; H; 5.06. Found: C, 52.18; H; 5.40.

Example 41

4-(1H-Imidazol-4-yl-methyl-quinoline dihydrochloride

Step A. Acetic acid-[2-(tert-Butyldimethylsilyl)-1-dimethylsulfamoyl-1H-imidazol-4-yl]-quinolin-4-yl-methyl ester. To 2-(tert-Butyldimethylsilyl)- 4-(hydroxyquinolin-4-yl-methyl)-imidazole-1-sulfonic acid dimethylamide (example 8, step A) (0.750 g, 1.62 mmol) in 8 ml of anhydrous toluene at 0° C., pyridine (0.16 ml, 1.94 mmol) was added followed by acetyl chloride (0.14 ml, 1.94 mmol). The solution was stirred at room temperature for two hours. It was cooled to 0° C. and ice cubes were added. The reaction mixture was partitioned between toluene (5 ml) and water (5 ml). The organic layer was dried over sodium sulfate, filtered, concentrated under reduced pressure and column purified (hexanes:EtOAc; 1:4) to give 0.84 g (100%) of the product.

Step B. 4-Quinolin-4-yl-methyl-imidazole-1-sulfonic acid dimethylamide. To Acetic acid-[2-(tert-Butyldimethylsilyl)-1-dimethylsulfamoyl-1H-imidazol-4-yl]-quinolin-4-yl-methyl ester (0.895 g, 1.72 mmol) in 10 ml of ethanol, 0.3 g of palladium on carbon (10%) was added and the solution hydrogenated at 40 psi for 18 hours. The solution was filtered over celite and concentrated under reduced pressure to give 0.190 g (53%) of the product as a syrup.

Step C. 4-(1H-Imidazol-4-yl-methyl)-quinoline. To 4-Quinolin-4-yl-methyl-imidazole-1-sulfonic acid dimethylamide (0.16 g, 0. 765 mmol), 7 ml of 1.5N HCl was added and the solution refluxed for two hours. The reaction mixture was concentrated, partitioned between water (10 ml) and EtOAc (2×10 ml). The organic layer was dried over sodium sulfate, filtered , concentrated and column purified ($CH_2Cl_2$: MeOH: methanol-$NH_3$(1.0M); (4.5:0.25:0.25) to yield 0.080 g (5%) of the product as a syrup.

Step D. 4-(1H-Imidazol-4-yl-methyl)-quinoline dihydrochloride. To 4-(1H-Imidazol-4-yl-methyl)-quinoline (0.08 g, 0.382 mmol) in 5 ml methanol, 3 ml of HCl in dioxane was added and the reaction mixture was concentrated under reduced pressure to give 0.107 g, (100%) of the product as a solid: m.p. >300° C.; Anal. Calcd. for $C_{13}H_{13}N_3Cl_2$ 1.0 mole $H_2O$: C, 52.02; H, 5.04; N 14.00. Found: C, 52.00; H, 4.81; N, 14.04.

Example 42

4-(1H-Imidazol-4-yl-methyl)-isoquinoline dihydrochloride

Step A. 2-(tert-Butyldimethylsilyl)-4-(hydroxyisoquinolin-4-yl-methyl)-imidazole-1-sulfonic acid dimethylamide. This compound was prepared according to experimental conditions outlined in example 39, step A, starting with isoquinoline-4-carbaldehyde (Gilman, H. et al. *J. Org. Chem.* 1957, 22, 565.) and N,N-dimethylsulfamoyl-2-(tert-butyldimethylsilyl)imidazole (Chadwick, D. J. et al. *J.Chem.Soc.Perkin Trans. I.* 1984, 481).

Step B. 2-(tert-Butyldimethylsilyl)-4-(chlorosoquinolin-4-yl-methyl) -imidazole-1-sulfonic acid dimethylamide. This compound was prepared from 2-(tert-Butyldimetiylsilyl)-4-(hydroxyisoquinolin-4-yl-methyl)-imidazole-1-sulfonic acid dimethylamide following experimental conditions outlined in example 33, step B.

Step C. 4-Isoquinolin-4-yl-methyl-midazole-1-sulfonic acid dimethyl amide. To 2-(tert-Butyldimethylsilyl)-4-(chloroisoquinolin-4-yl-methyl)-imidazole-1-sulfonic acid dimethylamide (0.150 g, 0.312 mmol) in 0.6 ml acetic acid (0.5 mmol), zinc dust (0.300 g, 5.55 mmol) was added and the solution stirred for 24 hours at room temperature. It was neutralized with ammonium hydroxide, EtOAc (20 ml) was added to the solution and filtered. The filtrate was partitioned between ethyl acetate and water (10 ml). The organic layer was dried over sodium sulfate, filtered and concentrated. Purification by column chromatography (EtOAc:MeOH; 4:1) gave 0.075 g (74%) of the product as a syrup.

Step D. 4-(1H-Imidazol-4-yl-methyl)-isoquinoline. To 4-Isoquinolin-4-yl-methyl-imidazole-1-sulfonic acid dimethyl amide (0.110 g, 0.312 mmol), 7 ml of 1.5N HCl was added and the solution refluxed for two hours. The reaction mixture was concentrated, partitioned between water 10 ml) and EtOAc (2×10 ml). The organic layer was dried over sodium sulfate, filtered , concentrated and column purified ($CH_2Cl_2$: MeOH: methanol-$NH_3$ (1.0M) (4.5:0.25:0.25) to yield 0.0528 g (81%.) of the product as a syrup.

Step E. 4-(1H-Imidazol-4-yl-methyl)-isoquinoline dihydrochloride. To 4-(1H-Imidazol-4-yl-methyl)-isoquinoline (0.053 g, 0.253 mmol) in 5 ml methanol, 3 ml of HCl in dioxane was added and the reaction fixture was concentrated under reduced pressure to give 0.071 g,(100%) of the product as a solid. Anal. Calcd. for $C_{13}H_{13}N_3Cl_2$ 1.3 mole $H_2O$: C, 51.10; H, 5.15; N, 13.75. Found: C, 51.27; H, 4.97; N, 13.54.

Example 43

1-(1H-Imidazol-4-yl-methyl)-isoquinoline dihydrochloride

Step A. 4-(1H-Imidazol-4-yl-methyl)-isoquinoline. This compound was prepared according to experimental conditions outlined in example 42, starting from isoindolone-1-carbaldehyde (F.Minisci et al. *J. Org. Chem.* 1986, 51, 536).

Step B. 1-(1H-Imidazol-4-yl-methyl)-isoindolone dihydrochloride. To 1-(1H-Imidazol-4 yl-methyl)-isoindolone (0.124 g, 0.592 mmol) in 5 ml methanol, 3 ml of HCl in dioxane was added and the reaction nixture was concentrated under reduced pressure to give 0.127 g, (74%) of the product as a pale yellow solid which was recrystallized from isopropanol-ether: m.p. 240°–242° C.; Anal. Calcd. for $C_{13}H_{11}N_3Cl_2$0.6 mole $H_2O$: C, 53.2; H, 4.89. Found: C, 53.30; H, 5.04.

Example 44

4-(1H-Imidazol-4-yl-methyl)-3-methylisoquinoline dihydrochloride

Step A. 4-Bromo-3-methylisoquinoline. To 3-methylisoquinoline (0.500 g, 3.49 mmol) in 1 ml nitrobenzene, bromine (0.196 ml, 3.84 mmol) was added and the contents heated in a sealed tube at 180° C. for 4 hours. The solution was cooled to room temperature, neutralized with solid sodium carbonate (pH=8) and extracted with ethyl acetate (2×20 ml). The organic layer was dried over sodium sulfate, filtered, concentrated and column purified (hexane:EtOAc; 4.5:0.5) to give 0.560 g (72%) of the product as syrup.

Step B. 3-methylisoquinoline-4-carbaldehyde. To a solution of n-BuLi (2.5M, 0.869 ml, 2.17 mmol) ) in 10 ml anhydrous THF at −50° C., 4-bromo-3-methylisoquinoline (0 460 g, 2.07 mmol) was added. After 10 minutes of stirring, DMF (0.32 g, 4.14 mmol) was added to the solution. The reaction mixture was allowed to stir at −50° C. for 20 minutes and then at room temperature for 15 minutes. 5 ml of 1N HCl was added and the solution was stirred for another 5 minutes. The reaction mixture was neutralized with saturated solution of $NaHCO_3$(25 ml) and partitioned between ethylacetate (2×20 ml) and water (10 ml). The organic layer was dried over sodium sulfate, filtered, concentrated and column purified (hexane:EtOAc; 3:2) to give 0.151 g (43%) of tle product as a syrup.

Step C. 4-(1H-Imidazol-4-yl-methyl)-3-methylisoquinoline. This compound was prepared from 3-methylisoquinoline-4-carbaldehyde employing reaction conditions outlined in example 42. Yield 0.042 g (81%).

Step D. 4-(1H-Imidazol-4-yl-methyl)-3-methylisoquinoline dihydrochloride. To 4-(1H-Imidazol-4-yl-methyl)-3-methylisoquinoline (0.042 g, 1.88 mmol) in 5 ml methanol, 3 ml of HCl in dioxane was added and the reaction mixture was concentrated under reduced pressure to give 0.042, (76%) of the product as a pale yellow solid which was recrystallized from isopropanol-ether. m.p. 160°–165° C.; Anal. Calcd. for $C_{14}H_{13}N_3Cl_2$ 1.1 mole $H_2O$: C, 53.21; H, 5.49. Found C, 53.02; H, 5.75.

It is understood that additional compounds may be synthesized under the general synthetic schemes referred to herein using appropriately substituted starting materials.

Example 45

As a specific embodiment of an oral composition of a compound of this invention, 100 mg of one of the compounds described herein is formulated with sufficient finely divided lactose to provide a total amount of 580 to 590 mg to fill a size O hard gel capsule.

Pharmacological profiles of the compounds at cloned human α adrenergic receptors Binding and functional assays were performed using stably transfected cells expressing human α adrenergic receptors. Equilibrium competition binding assays were performed with membrane preparations from cultured LM(tk-) cells stably transfected with the cloned human adrenoceptor subtypes except for $α_{2b}$, which was expressed in Y-1 cells, using [$^3$H]prazosin for $α_1$ receptors and [$^3$H] rauwolscine for $α_2$ receptors.

Protocol for the determination of the potency of ligands

The activity of the compounds at the different receptors was determined in vitro using cultured cell lines, each selectively expressing only one α adrenergic receptor subtype ($α_{1a}$, $α_{1b}$, $α_{1c}$, $α_{2a}$, or $α_{2c}$). These cell lines were prepared by transfecting cloned cDNA or cloned genomic DNA or constructs containing both genomic DNA and cDNA encoding the human α adrenergic receptors as described below.

Human $α_{2a}$ Adrenergic Receptor: The entire coding region of $α_{2a}$ (1350 bp), including 1.0 kilobasepairs of 5' untranslated sequence (5'UT) and 100 bp of 3' untranslated sequence (3'UT), was cloned into the SmaI site of the eukaryotic expression vector pCEXV-3. The insert housing his coding region was a 2.5 kb Kpn1/HindIII human placenta genomic fragment which was end-blunted by either $T_4$ polymerase or Klenow fragment of DNA polymerase. Stable cell lines were obtained by co-transfection with the plasmid pGCcos3neo (plasmid containing the $α_{2a}$ receptor gene) and the plasmid pGCcos3neo (plasmid containing the aminoglycoside transferase gene) into LM(tk-), CHO, and NIH3T3 cells, using calcium phosphate technique. The cells were grown in a controlled environment (37° C., 5% $CO_2$) as monolayers in Dulbecco's modified Eagle's Medium (GIBCO, Grand Island, N.Y.) containing 25 mM glucose and supplemented with 10% bovine calf serum, 100 units/mL penicillin g, and 100 mg/mL streptomycin sulfate. Stable clones were then selected for resistance to the antibiotic G-418 (1 mg/mL), and membranes were harvested and assayed for their ability to bind [$^3$H]rauwolscine as described below (see "Radioligand Binding Assays").

Human $α_{2b}$ Adrenergic Receptor: The entire coding region of $α_{2b}$ (1350 bp), including 393 bp of 5' untranslated sequence and 11 bp of 3' untranslated sequence, was cloned into the eukaryotic expression vector pcEXV-3. Stable cell lines were selected as described above.

Human $α_{2c}$ Adrenergic Receptor: The entire coding region of $α_{2c}$ (1383 bp), including 2 bp of 5' UT and 400 bp of 3' UT, was cloned into the Small site of the eukaryotic expression vector pCEXV-3. The insert housing this coding region was a 1.8 kb Ncol/EcoRI human spleen genomic fragment which was end-blunted by either $T_4$ polymerase or Klenow fragment of DNA polymerase. Stable cell lines were selected as described above.

Stable cell lines expressing the human $α_2$ adrenergic receptors described above as well as stable cell lines expressing the human $α_1$ adrenergic receptors have been deposited with the American Type Culture Collection (ATCC), 12301 Parklawn Drive, Rockville, Md., 20852, U.S.A., under the provisions of the Budapest Treaty for the International Recognition of the Deposit of Microorganisms for the Purposes of Patent Procedure. The cell line expressing the human $α_{2a}$ receptor is designated L-$α_{2A}$ and was deposited on Nov. 6, 1992, under ATCC Accession Number CRL-11180. The cell line expressing the human $α_{2b}$ receptor is designated L-NGC-$α_{2B}$ and was deposited on Oct. 25, 1989 under ATCC Accession Number CRL-10275. The cell line expressing the human $α_{2c}$ receptor is designated L-$α_{2C}$ and was deposited on Nov. 6, 1992, under ATCC Accession Number CRL-11181.

The cell line expressing the human $α_{1a}$ receptor is designated L-$α_{1A}$ and was deposited on Sep. 25, 1992, under ATCC Accession Number CRL-11138. The human $α_{1a}$ receptor is now known as the "$α_{1d}$" receptor due to a nomenclature change by the IUPHAR Nomenclature Committee, as outlined in the 1995 Receptor and Ion Channel Nomenclature Supplement (Watson and Girdlestune, 1995). The cell line expressing the human $α_{1b}$ receptor is designated L-$α_{1B}$ and was deposited on Sep. 29, 1992 under ATCC Accession Number CRL-11139. The cell line expressing the human $α_{1c}$ receptor is desicnated L-$α_{1C}$ and was deposited on Sep. 25, 1992, under ATCC Accession Number CRL-11140. The human $α_{1c}$ receptor was also renamed by the IUPHAR Nomenclature Committee and is now known as the "$α_{1a}$" receptor.

Radioligand Binding Assays: The stable cell lines described above were scraped from culture flasks into 5 mL of 5 mM Tris-HCl, 5 nM EDTA, pH 7.5, and lysed by sonication. The cell lysates were centrifuged at 1,000 rpm for 5 min. at 4° C., and the supernatant was centrifuged at 30,000×g for 20 min. at 4° C. The pellet was suspended in 50 mM Tris-HCl, 1 mM MgCl$_2$, and 0.1% ascorbic acid at pH 7.5. Binding of the α$_2$ antagonist [$^3$H]rauwolscine (0.5 nM) or the a$_1$ antagonist [$^3$H]prazosin (0.5 nM) to membrane preparations of LM(tk-) cells was done in a final volume of ).25 mL and incubated at 37° C. for 20 min. Nonspecific binding was determined in the presence of 10 mM phentolamine. The reaction was stopped by filtration through GF/B filters using a cell harvester. Inhibition experiments routinely consisting of 7 concentrations of the tested compounds were analyzed using a non-linear regression curve-fitting computer program to obtain Ki values.

Measurement of α$_2$ Agonist Activity: The agonist activity (expressed as pEC$_{50}$) was measured as a function of the ability to inhibit the forskolin-stimulated synthesis of cyclic adenosine monophosphate cAMP). The stably transfected cells were incubated in Ham's F10 with 5 mM theophylline, 10 mM HEPES, 17 mM pargyline, and/or appropriate concentrations of forskolin for 20 min. at 370° C. in 5% CO$_2$. The tested compounds were then addel to a final concentration of 0.001 nM to 1 mM and incubated for an additional 15 min. at 37° C. in 5% CO$_2$. The medium was aspirated and the reaction was stopped by the addition of 100 mM HCl. To demonstrate competitive antagonism, a dose-response curve for norepinephrine was obtained in parallel using a fixed dose of norepinephrine (0.32 mM). The plates were stored at 4° C. for 15 min. and assayed to determine the linear concentration of cAMP. The appropriate dilution was interpolated from the standard curve of cold cAMP. The assessment of cAMP formation was determined by radioimmunoassay (cAMP radioimmunoassay kit; Advanced magnetics, Cambridge, Mass.). Radioactivity was quantified using a Packard COBRA Auto Gamma counter equipped with data reduction software.

Binding affinities were measured for the compounds of the invention at the six α adrenergic receptor subtypes described above. The compounds were found to be α$_2$ selective agonists. The compounds were also found to exhibit weak binding to the α$_1$ receptors relative to the binding of the compounds to the α$_2$ receptors. Table 1 shows the binding and functional activities of selected compounds at cloned human α$_2$ adrenergic receptors.

TABLE 1

Binding and Functional Activities at Cloned Human α$_2$ Adrenoceptors (IA = Intrinsic Activity).

| Compound | α$_{2a}$ | | α$_{2b}$ | | α$_{2c}$ | |
|---|---|---|---|---|---|---|
| | pKi | pEC$_{50}$ (IA) | pKi | pEC$_{50}$ (IA) | pKi | pEC$_{50}$ (IA) |
| Medetomidine | 8.62 | 9.01 (1.00) | 8.63 | 9.02 (1.00) | 8.27 | 8.83 (1.00) |
| UK-14,304 | 8.15 | 9.20 (1.00) | 7.44 | 6.75 (1.00) | 7.03 | 8.23 (1.00) |
| Example 1 | 8.94 | 7.83 (0.48) | 8.54 | 7.44 (0.53) | 7.86 | 7.94 (1.00) |
| Example 21 | 7.30 | 6.41 (0.58) | 6.78 | 5.71 (0.55) | 6.34 | 7.79 (1.00) |
| Example 29 | 7.83 | 7.80 (1.00) | 7.29 | 7.04 (0.40) | 6.60 | 7.86 (1.00) |
| Example 30 | 7.75 | 8.53 (1.00) | 7.44 | 6.83 (0.43) | 6.51 | 8.20 (1.00) |
| Example 36 | 8.57 | 5.00 (0.00) | 7.39 | 5.55 (0.13) | 7.79 | 8.14 (0.77) |

What is claimed is:

1. A compound having the structure:

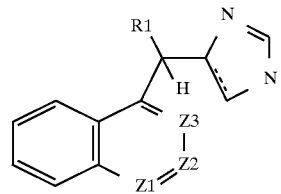

wherein each of Z1, Z2 and Z3 is N or CR$_2$, with the proviso that either one of Z1, Z2 or Z3 is N and the others of Z1, Z2 or Z3 are CR$_2$, or both Z1 and Z3 are N and Z2 is CR$_2$;

wherein R$_1$ is H; F; straight chained or branched C$_1$–C$_4$ alkyl, C$_1$–C$_4$ monofluoroalkyl or C$_1$–C$_4$ polyfluoroalkyl; straight chained or branched C$_1$–C$_4$ alkoxy, —OH; or —(CH$_2$)$_q$OH;

wherein each R$_2$ is independently H; F; Cl; Br; I; —NO$_2$, —CN; straight chained or branched C$_1$–C$_4$ alkyl; C$_1$–C$_4$ monofluoroalkyl or C$_1$–C$_4$ polyfluoroalkyl; straight chained or branched C$_1$–C$_4$ alkoxy; —OH; —(CH$_2$)$_q$OH; —COR$_4$; CO$_2$R$_4$; CONHR$_4$; phenyl; or benzyl;

wherein each R$_4$ is independently H; straigh chained or branched C$_1$–C$_4$ alkyl, C$_1$–C$_4$ monofluoroalkyl or C$_1$–C$_4$ polyfluoroalkyl; or phenyl; and wherein q is each independently 0, 1, 2 or 3;

or a pharmaceutically acceptable salt thereof.

2. The compound of claim 1, wherein the compound comprises the (+) enantiomer.

3. The compound of claim 1, wherein the compound comprises the (−) enantiomer.

4. The compound of claim 1, wherein two of Z1, Z2 and Z3 are CR$_2$ and the other is N.

5. The compound of claim 4, wherein at least one R$_2$ is methyl or phenyl.

6. The compound of claim 4, wherein R$_1$ is C$_1$–C$_3$ alkyl, C$_1$–C$_3$ alkoxy, or —OH.

7. The compound of claim 6 having the structure:

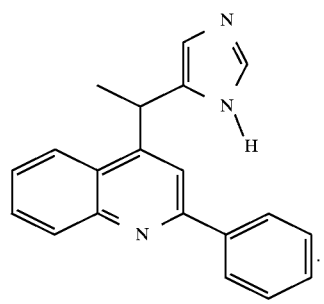

8. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

PATENT NO. : 5,866,579
DATED : February 2, 1999
INVENTOR(S) : Wai. C. Wong, et al.

It is certified that error appears in the above-identified patent and that said Letters Patent is hereby corrected as shown below:

Column 1,
Line 5: "ace" should read -- are --
Line 24: "canr" should read -- can --
Line 25: "disinct" should read -- distinct --
Line 27: "antagorists" should read -- antagonists --
Line 52: "P." should read -- A. --.

Column 2,
Line 3: "including" should read -- include --
Line 5: "ischemia" should read -- ischemia, --
Line 8: "midazoline" should read -- imidazoline --
Line 27: "omposition" should read -- composition --
Line 47: "NO" should read -- $NO_2$ --

Column 3,
Line 25: "otters" should read -- others --
Line 28: "monofluorocalkyl" should read -- monofluoroalkyl --
Line 32: "NO" should read -- $NO_2$ --
Line 35: "COR" should read --$COR_4$ --

Column 4,
Line 49: "otiers" should read -- others --

Column 5,
Line 16: "NO" should read -- $NO_2$ --
Line 28: "monofluoroalky" should read -- monofluoroalkyl --

Column 6,
Line 33 "NO" should read -- $NO_2$ --
Line 60 "alky" should read -- alkyl --

Column 7,
Line 16 "branchec" should read -- branched --
Line 27 "monofluoralkyl or polyfloroakly" should read -- $C_1$-$C_4$ monofluoroalkyl $C_1$-$C_4$ polyfluoroakly --
Line 30 "thereof" should read -- thereof. --
Line 46 "ethylene" should read -- methylene --
Line 63 "R" should read -- $R_2$ --
Line 66 "$R_2$" should read -- $R_1$ --

UNITED STATES PATENT AND TRADEMARK OFFICE
CERTIFICATE OF CORRECTION

PATENT NO.  : 5,866,579
DATED       : February 2, 1999
INVENTOR(S) : Wai. C. Wong, et al.

It is certified that error appears in the above-identified patent and that said Letters Patent is hereby corrected as shown below:

Column 9,
Line 18 "are" should read -- and --
Line 21 "ethylendlamine" should read -- ethylenediamine --

Column 10,
Line 7 "in. ramuscular" should read -- intramuscular --
Line 37 "ablets" should read "tablets"
Line 52 "Pluroric" should read -- Pluronic --
Line 53 "Thimeosal" should read -- Thimerosal --
Line 61 "erythrocyt" should read -- erythrocyte --
Line 62 " he" should read -- the --
Line 63 "elease" should read -- release --

Column 11,
Line 9 "Include" should read -- include --
Line 12 "polxamines" should read -- poloxamines --
Line 32 "he" should read -- the --

Column 12,
Line 65 "a" should read -- $\alpha_2$ --
Line 27 "ar" should read -- an --

Column 13,
Line 40 "$CH_2 \; CH_2 \; (CH_2)_q OHCOR_4$" should read -- $CH_2 \; CH_2 \; (CH_2)_q OH; \; COR_4$ --
Line 51 "thereof 078665795" should read -- thereof. --
Line 52 "or" should read -- for --

Column 14,
Line 7 "$R_1$" should read -- $R_2$ --
Line 19 "ore" should read -- one --
Line 25 "obtain d" should read -- obtained --

Column 16,
Line 48 "Scheie" should read -- scheme --

Column 19,
Line 45 "cried" should read -- dried --
Line 43 "6.77" should read -- 66.77 --

UNITED STATES PATENT AND TRADEMARK OFFICE
CERTIFICATE OF CORRECTION

PATENT NO. : 5,866,579
DATED : February 2, 1999
INVENTOR(S) : Wai. C. Wong, et al.

It is certified that error appears in the above-identified patent and that said Letters Patent is hereby corrected as shown below:

Line 53 "chromatographec" should read -- chromatographed --
Line 65 "Dibrormo" should read -- Dibromo --; "arninoindane" should read
-- aminoindane --

Column 20,
Line 39 "queous" should read aqueous --
Line 45 "basined" should read -- basified --
Line 61 "1.38 9g" should read -- 1.38g --

Column 21,
Line 38 "basined" should read -- basified --
Line 52 "tetralln." should read -- tetralin --
Line 57 washec should read -- washed --

Column 22,
Line 33 "ir" should read -- in --
Line 50 "methoxyimin" should read -- methoxyimino --

Column 23,
Line 4 "1,2,3,4-Tetrhydro-7-" should read -- 1,2,3,4-Tetrahydyro-1 --
Line 21 "was" should read -- wis --
Line 44 "reated" should read -- treated --
Line 50 "MEDH" should read -- MeOH --
Line 53 "are" should read -- and --

Column 24,
Line 14 "basined" should read -- basified --

Column 25,
Line 3 "residle" should read -- residue --
Line 66 "chromarographed" should read -- chromatographed --

Column 26,
Line 13 "2.53mm(l) should read -- 2.53 mmol --
Line 24 "basined" should read -- basified --
Line 27 "isopropy" should read -- isopropyl --
Line 35 "reated" should read -- treated --
Line 47 "mmcl" should read -- mmol --
Line 51 "dinitio" should read -- dinitro --
Line 66 "residie" should read -- residue --

UNITED STATES PATENT AND TRADEMARK OFFICE
CERTIFICATE OF CORRECTION

PATENT NO.    : 5,866,579
DATED         : February 2, 1999
INVENTOR(S)   : Wai. C. Wong, et al.

It is certified that error appears in the above-identified patent and that said Letters Patent is hereby corrected as shown below:

Column 27,
Line 14 "quinolne" should read -- quinoline --
Line 19 "chromatographec" should read -- chromatographed --
Line 22 "3-Amino-5,6,7,8-tetrahydro-6,6-dimethylquilno" should read -- 3-Amino-5,6,7,8-tetrahydro-6,6-dimethylquinoline --
Line 29 "2- (5,6,7,8-tetrahydro-8,8-dimethyl-quinolin-3-yl)iamino-2-imidazoline" should read -- 2- (5,6,7,8-tetrahydro-8,8-dimethyl-quinolin-3-yl)amino-2-imidazoline --
Line 43, "(R)-2- (5,6,7,8-tetrahydro-6,8-dimethymethano-quinolin-3-yl)iamino-2-imidazoline" should read -- (R)-2- (5,6,7,8-tetrahydro-6,8-dimethylmetano-quinolin-3-yl)amino-2-imidazoline --
Line 59 "basined" should read -- basified --
Line 62 "5,6,7, 8-tetrahydro-6,8-dimethylmethano-7quinolin-3-yl)amino-2-imidazoline should read -- 5,6,7, 8-tetrahydro-6,8-dimethylmethano-quinolin-3-yl)amino-2-imidazoline
Line 66 "or" should read -- for --

Column 28,
Line 7 "14.36" should read -- 14.86 --
Line 12 "2-(Ethyl-6,78-tetrahydro-1,6-naphthyrid-3-yl)amino-2-imidazoline" should read -- 2-(6-Ethyl-5,6,78-tetrahydro-1,6-naphthyrid-3-yl)amino-2-imidazoline --
Line 21 "3-Amino-6-ethyl-5,6,7,8-tetrahydro-1,6-anphthyridine" should read -- 3-Amino-6-ethyl-5,6,7,8-tetrahydro-1,6-naphthyridine --
Line 35 "ove" should read -- over --
Line 40 "recrystllized" should read -- recrystalllized --

Column 29,
Line 19 "ovei" should read -- over --
Line 21 "(0.623 g, 63% yield" should read -- (0.623 g, 63% yield).
Line 51 "wa" should read -- was --
Line 57 ".8" should read -- .84 --

Column 30,
Line 27 "cut" should read -- out --
Line 40 "yelloo" should read -- yellow --
Line 55 "chromatocraphed" should read -- chromatographed --
Line 67 "4.7 mmol" should read -- 4.67mmol --

UNITED STATES PATENT AND TRADEMARK OFFICE
CERTIFICATE OF CORRECTION

PATENT NO. : 5,866,579
DATED : February 2, 1999
INVENTOR(S) : Wai. C. Wong, et al.

It is certified that error appears in the above-identified patent and that said Letters Patent is hereby corrected as shown below:

Column 31,
Line 1 "(3mL." should read -- (3mL) --
Line 2 "an" should read -- in --
Line 5 "ethiol" should read -- ethanol --
Line 20 "porticol" should read -- portion --
Line 21 "pel" should read -- gel --
Line 36 "cnromatographed" should read -- chromatographed --
Line 38 "ethaiol" should read -- ethanol --

Column 32,
Line 13 "2-(2,3-Cyclopenteno-1-oxido-5-pyri(yl)amino-2-imidazoline" should read -- 2-(2,3-Cyclopenteno-1-oxido-5-pyridyl)amino-2-imidazoline --
Line 55 "removei" should read -- removed --
Line 56 "chromatograrhy" should read -- chromatography --

Column 33,
Line 7 "(0.28 g)" should read -- (0.028 g) --
Line 27 "residie" should read -- residue --
Line 31 "intermeciate" should read -- intermediate --
Line 33, "th4ophosgene" should read -- thiophosgene --

Column 34,
Line 3. "proiuct" should read -- product --
Line "(0.3mL)." should read -- (0.8 mL). --
Line 18, "(0 178g 0.61 mml)" should read -- (0.178 g, 0.61 mmol) --
Line 62 "r ixture" should read -- mixture --

Column 35,
Line 27 "iixture" should read -- mixture --
Line 36 "aas" should read -- was --

Column 36,
Line 5 "1.54 a" should read -- 1.54 g --

Column 37,
Line 5 "isopropaanol-ether" should read -- isopropanol-ether --

UNITED STATES PATENT AND TRADEMARK OFFICE
CERTIFICATE OF CORRECTION

PATENT NO. : 5,866,579
DATED : February 2, 1999
INVENTOR(S) : Wai. C. Wong, et al.

It is certified that error appears in the above-identified patent and that said Letters Patent is hereby corrected as shown below:

Column 38,
Line 25 "4-quinolinecarbaldehyce" should read -- 4-quinolinecarbaldehyde --
Line 41 "(1H-Imidazol-4-yl)-quinolin-4-yl-metanol dihydrochlcride" should read -- (1H-Imidazol-4-yl)-quinolin-4-yl-methanol dihydrochloride --
Line 44 "0.33 g" should read -- 0.033 g --

Column 39,
Line 9 "4-[1H-Imadazol-4-yl)-methoxymethil]quinolinedihydrochloride" should read -- 4-[1H-Imadazol-4-yl)-methoxymethil]quinolinedihydrochloride --
Line 51 "(5%)" should read -- 51% --

Column 40,
Line 7 "2-(tert-Butyldimethylsilyl)-4-chlorosoquinolin-4-yl-methyl -imidazole-1-sulfonic acid dimethylamide" should read -- 2-(tert-Butyldimethylsilyl)-4-chloroisoquinolin-4-yl-methyl-imidazole-1-sulfonic acid dimethylamine --
Line 10 " 2-(tert-Butyldimetiylsilyl-4-(hydroxyisoquinolin-4-yllmethyl)-1-sulfonic acid dimethylamide" should read -- 2-(tert-Butyldimetiylsilyl-4-(hydroxyisoquinolin-4-yllmethyl)-1-sulfonic acid dimethylamide --
Line 13 "4-Isoquinolin-4-yl-methyl-midazole-1-sulfonic acid dimethyl amide" should read -- 4-Isoquinolin-4-yl-methyl-imidazole-1-sulfonic acid dimethyl amide --
Line 36 "fixture" should read -- mixture --
Line 47 "isoindolone-1-carbaldehyde" should read -- isoquinoline-1-carbaldehyde --
Line 49 "1-(1H-Imidazol-4-yl-methyl)-isoindolone dyhydrochloride" should read -- 1-(1H-Imidazol-4-yl-methyl)-isoindoline dyhydrochloride --
Line 56 "53.2" should read -- 53.29 --

Column 41,
Line 9, "(0 460 g, 2.07 mmol) should read -- (0.460 g, 2.07 mmol) --
Line 58 "($\alpha_{1a}, \alpha_{1b}, \alpha_{1c}, \alpha_{2a}, \alpha_{2c}$)" should read --"($\alpha_{1a}, \alpha_{1b}, \alpha_{1c}, \alpha_{2a}, \alpha_{2b}, \alpha_{2c}$)

UNITED STATES PATENT AND TRADEMARK OFFICE
CERTIFICATE OF CORRECTION

PATENT NO. : 5,866,579
DATED : February 2, 1999
INVENTOR(S) : Wai. C. Wong, et al.

It is certified that error appears in the above-identified patent and that said Letters Patent is hereby corrected as shown below:

<u>Column 42,</u>
Line 1 "his" should read -- this --
Line 25 "Small" should read -- Sma1 --
Line 53 "Girdlestune" should read -- Girdlestone --
Line 57 "desicnated" should read -- designated --

<u>Column 43,</u>
Line 18 "370°" should read -- 37° --

Signed and Sealed this

Twenty-seventh Day of November, 2001

Attest:

*Attesting Officer*

NICHOLAS P. GODICI
*Acting Director of the United States Patent and Trademark Office*